(12) United States Patent
Hinman et al.

(10) Patent No.: US 7,632,946 B2
(45) Date of Patent: Dec. 15, 2009

(54) NAPHTHYRIDINE-BASED ANTIBACTERIAL COMPOSITIONS

(75) Inventors: Mira M Hinman, Libertyville, IL (US); Teresa A. Rosenberg, Gurnee, IL (US); Rolf Wagner, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 55 days.

(21) Appl. No.: 11/051,909

(22) Filed: Feb. 4, 2005

(65) Prior Publication Data

US 2007/0088040 A1 Apr. 19, 2007

Related U.S. Application Data

(60) Provisional application No. 60/542,808, filed on Feb. 6, 2004.

(51) Int. Cl.
*C07D 265/34* (2006.01)
*C07D 491/00* (2006.01)
*A61K 31/50* (2006.01)

(52) U.S. Cl. .................. 544/101; 544/345; 514/250

(58) Field of Classification Search ............... 544/101, 544/345; 514/250
See application file for complete search history.

(56) References Cited

OTHER PUBLICATIONS

Nishimura et al J. Heterocyclic Chem. 1988, 25, 479-485.*

* cited by examiner

*Primary Examiner*—Rita J Desai
*Assistant Examiner*—John Mabry
(74) *Attorney, Agent, or Firm*—Michael J. Ward

(57) ABSTRACT

Bacterial protein synthesis-inhibiting compounds having formula (I)

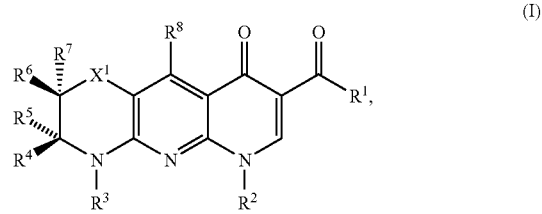

(I)

and salts, prodrugs, and salts of prodrugs thereof, processes for making the compounds and intermediates in the processes, compositions containing the compounds, and methods of using the compounds are disclosed.

2 Claims, No Drawings

NAPHTHYRIDINE-BASED ANTIBACTERIAL COMPOSITIONS

This application claims the benefit of U.S. Provisional Application No. 60/542,808, filed Feb. 6, 2004.

FIELD OF THE INVENTION

This invention pertains to compounds which inhibit bacterial protein synthesis, processes for making the compounds and intermediates in the processes, compositions containing the compounds, and uses for the compounds.

BACKGROUND OF THE INVENTION

Because the effectiveness of many drugs currently available for treating bacterial infections can be compromised by the emergence of drug-resistant bacteria, novel antibacterials would be useful for their therapeutic value and their contribution to the antibacterial arts.

SUMMARY OF THE INVENTION

Accordingly, one embodiment of this invention pertains to compounds, and salts, prodrugs, salts of prodrugs, and metabolites thereof, which inhibit bacterial protein synthesis, the compounds having formula (I)

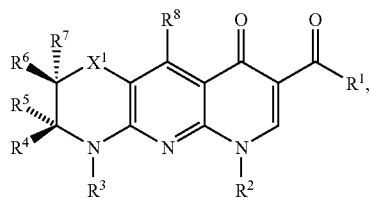

in which $R^1$ is —OH, —$OR^9$, —$NH_2$, —$NHR^9$, or —$N(R^9)_2$; $R^2$ is hydrogen, tert-butyl, —O(allyl), (4-methoxyphenyl)methyl, or (2,4-dimethoxyphenyl)methyl; one of $R^4$ or $R^5$ is hydrogen, $R^{10}$, —$C(O)R^{10}$, $R^{11}$, —$C(O)CH_2R^{11}$, $R^{12}$, —$C(O)CH_2R^{12}$, $R^{13}$, or —$C(O)R^{13}$, and the other is together with $R^3$ and is —$CH_2CH_2$—, —$CH_2CH_2CH_2$—, or —$CH_2CH_2CH_2CH_2$—, in which the —$CH_2CH_2$—, the —$CH_2CH_2CH_2$—, and the —$CH_2CH_2CH_2CH_2$— are unsubstituted or substituted with one $R^{10}$, $R^{11}$, $R^{12}$, $R^{13}$, —F, —Cl, —Br, —I, —OH, —$OR^{10}$, =O, —$N_3$, —$NH_2$, —$NHR^{10}$, —$N(R^{10})_2$, —$NHC(O)R^{10}$, —$N(R^{14})C(O)R^{10}$, —$NHSO_2R^{10}$, —$N(R^{14})SO_2R^{10}$, or —$OSO_2OR^{10}$ substituent; $R^6$ is hydrogen, $R^{15}$, —$C(O)R^{15}$, $R^{16}$, —$C(O)CH_2R^{16}$, $R^{17}$, —$C(O)CH_2R^{17}$, $R^{18}$, or —$C(O)R^{18}$; $R^7$ is hydrogen, $R^{15}$, —$C(O)R^{15}$, $R^{16}$, —$C(O)CH_2R^{16}$, $R^{17}$, —$C(O)CH_2R^{17}$, $R^{18}$, or —$C(O)R^{18}$; or $R^6$ and $R^7$ together are =O; $R^8$ is hydrogen, $R^{19}$, —OH, —$OR^{19}$, —$NH_2$, —$NHR^{19}$, —$N(R^{19})_2$, —$NHC(O)R^{19}$, —$NR^{20}C(O)R^9$, —$NHC(O)OR^{19}$, —$NR^{20}C(O)OR^{19}$, —$NHSO_2R^{19}$, —$NR^{20}SO_2R^{19}$, or $R^{21}$; $R^9$ is $C_1$-alkyl, $C_2$-alkyl, $C_3$-alkyl, $C_4$-alkyl, $C_5$-alkyl, $C_6$-alkyl, or $R^{9a}$; $R^{9a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{9b}$, —$NH_2$, —$NHR^{9b}$, —$N(R^{9b})_2$, phenyl, furanyl, or thiophenyl substituents; $R^{9b}$ is $C_1$-alkyl, $C_2$-alkyl, $C_3$-alkyl, $C_4$-alkyl, $C_5$-alkyl, or $C_6$-alkyl; $R^{10}$ is $C_1$-alkyl, $C_2$-alkyl, $C_3$-alkyl, $C_4$-alkyl, $C_5$-alkyl, $C_6$-alkyl, or $R^{10a}$; $R^{10a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{10b}$, —$NH_2$, —$NHR^{10b}$, —$N(R^{10b})_2$, or $R^{10c}$ substituents; $R^{10b}$ is $C_1$-alkyl, $C_2$-alkyl, $C_3$-alkyl, $C_4$-alkyl, $C_5$-alkyl, or $C_6$-alkyl; $R^{10c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{10d}$, —F, —Cl, —Br, —I, —CN, —OH, —$OR^{10d}$, —$NH_2$, —$NHR^{10d}$, —$N(R^{10d})_2$, —$NO_2$, —$CF_3$, —$OCF_3$, —$SR^{10d}$, —$S(O)R^{10d}$, —$SO_2R^{10d}$, —C(O)H, —$C(O)R^{10d}$, —C(O)OH, —$C(O)OR^{10d}$, —$C(O)NH_2$, —$C(O)NHR^{10d}$, —$C(O)N(R^{10d})_2$, or $R^{10e}$ substituents; $R^{10d}$ is $C_1$-alkyl, $C_2$-alkyl, $C_3$-alkyl, $C_4$-alkyl, $C_5$-alkyl, or $C_6$-alkyl; $R^{10e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{10f}$, —F, —Cl, —Br, —I, —CN, —OH, —$OR^{10f}$, —$NH_2$, —$NHR^{10f}$, —$N(R^{10f})_2$, —$NO_2$, —$CF_3$, —$OCF_3$, —$SR^{10f}$, —$S(O)R^{10f}$, —$SO_2R^{10f}$, —C(O)H, —$C(O)R^{10f}$, —C(O)OH, —$C(O)OR^{10f}$, —$C(O)NH_2$, —$C(O)NHR^{10f}$, or —$C(O)N(R^{10f})_2$ substituents; $R^{10f}$ is $C_1$-alkyl, $C_2$-alkyl, $C_3$-alkyl, $C_4$-alkyl, $C_5$-alkyl, or $C_6$-alkyl; $R^{11}$ is $C_2$-alkenyl, $C_3$-alkenyl, $C_4$-alkenyl, $C_5$-alkenyl, $C_6$-alkenyl, or $R^{11a}$; $R^{11a}$ is $C_2$-alkenyl, $C_3$-alkenyl, $C_4$-alkenyl, $C_5$-alkenyl, or $C_6$-alkenyl, each of which is substituted with one or two independently selected —$CF_3$, —$CF_2CF_3$, —F, —Cl, —Br, —I, —OH, —$OR^{11b}$, —$NH_2$, —$NHR^{11b}$, —$N(R^{11b})_2$, or $R^{11c}$ substituents; $R^{11b}$ is $C_1$-alkyl, $C_2$-alkyl, $C_3$-alkyl, $C_4$-alkyl, $C_5$-alkyl, or $C_6$-alkyl; $R^{11c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{11d}$, —F, —Cl, —Br, —I, —CN, —OH, —$OR^{11d}$, —$NH_2$, —$NHR^{11d}$, —$N(R^{11d})_2$, —$NO_2$, —$CF_3$, —$OCF_3$, —$SR^{11d}$, —$S(O)R^{11d}$, —$SO_2R^{11d}$, —C(O)H, —$C(O)R^{11d}$, —C(O)OH, —$C(O)OR^{11d}$, —$C(O)NH_2$, —$C(O)NHR^{11d}$, —$C(O)N(R^{11d})_2$, or $R^{11e}$ substituents; $R^{11d}$ is $C_1$-alkyl, $C_2$-alkyl, $C_3$-alkyl, $C_4$-alkyl, $C_5$-alkyl, or $C_6$-alkyl; $R^{11e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{11f}$, —F, —Cl, —Br, —I, —CN, —OH, —$OR^{11f}$, —$NH_2$, —$NHR^{11f}$, —$N(R^{11f})_2$, —$NO_2$, —$CF_3$, —$OCF_3$, —$SR^{11f}$, —$S(O)R^{11f}$, —$SO_2R^{11f}$, —C(O)H, —$C(O)R^{11f}$, —C(O)OH, —$C(O)OR^{11f}$, —$C(O)NH_2$, —$C(O)NHR^{11f}$, or —$C(O)N(R^{11f})_2$ substituents; $R^{11f}$ is $C_1$-alkyl, $C_2$-alkyl, $C_3$-alkyl, $C_4$-alkyl, $C_5$-alkyl, or $C_6$-alkyl; $R^{12}$ is $C_2$-alkenyl, $C_3$-alkenyl, $C_4$-alkenyl, $C_5$-alkenyl, $C_6$-alkenyl, or $R^{12a}$; $R^{12a}$ is $C_2$-alkenyl, $C_3$-alkenyl, $C_4$-alkenyl, $C_5$-alkenyl, or $C_6$-alkenyl, each of which is substituted with one or two independently selected —$CF_3$, —$CF_2CF_3$, —F, —Cl, —Br, —I, —OH, —$OR^{12b}$, —$NH_2$, —$NHR^{12b}$, —$N(R^{12b})_2$, or $R^{12c}$ substituents; $R^{12b}$ is $C_1$-alkyl, $C_2$-alkyl, $C_3$-alkyl, $C_4$-alkyl, $C_5$-alkyl, or $C_6$-alkyl; $R^{12c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{12d}$, —F, —Cl, —Br, —I, —CN, —OH, —$OR^{12d}$, —$NH_2$, —$NHR^{12d}$, —$N(R^{12d})_2$, —$NO_2$, —$CF_3$, —$OCF_3$, —$SR^{12d}$, —$S(O)R^{12d}$, —$SO_2R^{12d}$, —C(O)H, —$C(O)R^{12d}$, —C(O)OH, —C(O)$OR^{12d}$, —$C(O)NH_2$, —$C(O)NHR^{12d}$, —$C(O)N(R^{12d})_2$, or $R^{12e}$ substituents; $R^{12d}$ is $C_1$-alkyl, $C_2$-alkyl, $C_3$-alkyl, $C_4$-alkyl, $C_5$-alkyl, or $C_6$-alkyl; $R^{12e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{12f}$, —F, —Cl, —Br, —I, —CN, —OH, —$OR^{12f}$, —$NH_2$, —$NHR^{12f}$, —$N(R^{12f})_2$, —$NO_2$, —$CF_3$, —$OCF_3$, —$SR^{12f}$, —$S(O)R^{12f}$, —$SO_2R^{12f}$, —C(O)H, —$C(O)R^{12f}$, —C(O)OH, —C(O)$OR^{12f}$, —$C(O)NH_2$, —$C(O)NHR^{12f}$, or —$C(O)N(R^{12f})_2$ substituents; $R^{12f}$ is $C_1$-alkyl, $C_2$-alkyl, $C_3$-alkyl, $C_4$-alkyl, $C_5$-alkyl, or $C_6$-alkyl; $R^{13}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{13a}$, —F, —Cl, —Br, —I, —CN, —OH, —$OR^{13a}$, —$NH_2$, —$NHR^{13a}$, —$N(R^{13a})_2$, —$NO_2$, —$CF_3$, —$OCF_3$, —$SR^{13a}$, —$S(O)R^{13a}$, —$SO_2R^{13a}$, —C(O)H, —$C(O)R^{13a}$, —C(O)OH, —C(O)$OR^{13a}$, —$C(O)NH_2$, —$C(O)NHR^{13a}$, —$C(O)N(R^{13a})_2$, or $R^{13b}$ substituents; $R^{13a}$ is $C_1$-alkyl, $C_2$-alkyl, $C_3$-alkyl, $C_4$-alkyl, $C_5$-alkyl, or $C_6$-alkyl; $R^{13b}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{13c}$, —F, —Cl, —Br, —I, —CN, —OH, —$OR^{13c}$, —$NH_2$, —$NHR^{13c}$, —$N(R^{13c})_2$, —$NO_2$, —$CF_3$, —$OCF_3$, —$SR^{13c}$, —$S(O)R^{13c}$, —$SO_2R^{13c}$, —C(O)H, —$C(O)R^{13c}$, —C(O)OH, C(O)$OR^{13c}$, —$C(O)NH_2$, —$C(O)NHR^{13c}$, or —$C(O)N(R^{13c})_2$ substituents; $R^{13c}$ is $C_1$-alkyl, $C_2$-alkyl, $C_3$-alkyl, $C_4$-alkyl, $C_5$-alkyl, or $C_6$-alkyl; $R^{14}$ is $C_1$-alkyl, $C_2$-alkyl, $C_3$-alkyl, $C_4$-alkyl, $C_5$-alkyl, $C_6$-alkyl, or $R^{14a}$; $R^{14a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{14b}$, —$NH_2$, —$NHR^{14}$, —$N(R^{14b})_2$, or $R^{14c}$ substituents; $R^{14b}$ is $C_1$-alkyl, $C_2$-alkyl, $C_3$-alkyl, $C_4$-alkyl, $C_5$-alkyl, or $C_6$-alkyl; $R^{14c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{14d}$, —F, —Cl, —Br, —I, —CN, —OH, $OR^{14d}$, —$NH_2$, —$NHR^{14d}$, —$N(R^{14d})_2$, —$NO_2$, $CF_3$, —$OCF_3$, —$SR^{14d}$, —$S(O)R^{14d}$, —$SO_2R^{14d}$, —C(O)H, —$C(O)R^{14d}$, —C(O)OH, —C(O)$OR^{14d}$, —$C(O)NH_2$, —$C(O)NHR^{14d}$, —$C(O)N(R^{14d})_2$ or $R^{14e}$ substituents; $R^{14d}$ is $C_1$-alkyl, $C_2$-alkyl, $C_3$-alkyl, $C_4$-alkyl, $C_5$-alkyl, or $C_6$-alkyl; $R^{14e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{14f}$, —F, —Cl, —Br, —I, —CN, —OH, —$OR^{14f}$, —$NH_2$, —$NHR^{14f}$, —$N(R^{14f})_2$, —$NO_2$, —$CF_3$, —$OCF_3$, —$SR^{14f}$, —$S(O)R^{14f}$, —$SO_2R^{14f}$, —C(O)H, —$C(O)R^{14f}$, —C(O)OH, —C(O)$OR^{14f}$, —$C(O)NH_2$, —$C(O)NHR^{14f}$, or —$C(O)N(R^{14f})_2$ substituents; $R^{14f}$ is $C_1$-alkyl, $C_2$-alkyl, $C_3$-alkyl, $C_4$-alkyl, $C_5$-alkyl, or $C_6$-alkyl; $R^{15}$ is $C_1$-alkyl, $C_2$-alkyl, $C_3$-alkyl, $C_4$-alkyl, $C_5$-alkyl, $C_6$-alkyl, or $R^{15a}$; $R^{15a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{15b}$, —$NH_2$, —$NHR^{15b}$, —$N(R^{15b})_2$, or $R^{15c}$ substituents; $R^{15b}$ is $C_1$-alkyl, $C_2$-alkyl, $C_3$-alkyl, $C_4$-alkyl, $C_5$-alkyl, or $C_6$-alkyl; $R^{15c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{15d}$, —F, —Cl, —Br, —I, —CN, —OH, —$OR^{15d}$, —$NH_2$, —$NHR^{15d}$, —$N(R^{15d})_2$, —$NO_2$, —$CF_3$, —$OCF_3$, —$SR^{15d}$ $S(O)R^{15d}$, —$SO_2R^{15d}$, —C(O)H, —$C(O)R^{15d}$, —C(O)OH, —C(O)$OR^{15d}$, —$C(O)NH_2$, —$C(O)NHR^{15d}$, —$C(O)N(R^{15d})_2$, or $R^{15e}$ substituents; $R^{15d}$ is $C_1$-alkyl, $C_2$-alkyl, $C_3$-alkyl, $C_4$-alkyl, $C_5$-alkyl, or $C_6$-alkyl; $R^{15e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{15f}$, —F, —Cl, —Br, —I, —CN, —OH, —$OR^{15f}$, —$NH_2$, —$NHR^{15f}$, —$N(R^{15f})_2$, —$NO_2$, —$CF_3$, —$OCF_3$, —$SR^{15f}$, —$S(O)R^{15f}$, —$SO_2R^{15f}$, —C(O)H, —$C(O)R^{15f}$, —C(O)OH, —C(O)$OR^{15f}$, —$C(O)NH_2$, —$C(O)NHR^{15f}$, or —$C(O)N(R^{15f})_2$ substituents; $R^{15f}$ is $C_1$-alkyl, $C_2$-alkyl, $C_3$-alkyl, $C_4$-alkyl, $C_5$-alkyl, or $C_6$-alkyl; $R^{16}$ is $C_2$-alkenyl, $C_3$-alkenyl, $C_4$-alkenyl, $C_5$-alkenyl, $C_6$-alkenyl, or $R^{16a}$; $R^{16a}$ is $C_2$-alkenyl, $C_3$-alkenyl, $C_4$-alkenyl, $C_5$-alkenyl, or $C_6$-alkenyl, each of which is substituted with one or two independently selected —$CF_3$, —$CF_2CF_3$, —F, —Cl, —Br, —I, —OH, —$OR^{16b}$, —$NH_2$, —$NHR^{16b}$, —$N(R^{16b})_2$, or $R^{16c}$ substituents; $R^{16b}$ is $C_1$-alkyl, $C_2$-alkyl, $C_3$-alkyl, $C_4$-alkyl, $C_5$-alkyl, or $C_6$-alkyl; $R^{16c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{16d}$, —F, —Cl, —Br, —I, —CN, —OH, $OR^{16d}$, —$NH_2$, —$NHR^{16d}$, —$N(R^{16d})_2$, —$NO_2$, —$CF_3$, —$OCF_3$, —$SR^{16d}$, —$S(O)R^{16d}$, —$SO_2R^{16d}$, —C(O)H, —$C(O)R^{16d}$, —C(O)OH, —C(O)$OR^{16d}$, —$C(O)NH_2$, —$C(O)NHR^{16d}$, —$C(O)N(R^{16d})_2$, or $R^{16e}$ substituents; $R^{16d}$ is $C_1$-alkyl, $C_2$-alkyl, $C_3$-alkyl, $C_4$-alkyl, $C_5$-alkyl, or $C_6$-alkyl; $R^{16e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3- triazolyl, or thiophenyl ring, each of which is unsubstituted or substituted with one or two or three independently selected $R^{16f}$, —F, —Cl, —Br, —I, —CN, —OH, —$OR^{16f}$, —$NH_2$, —$NHR^{16f}$, —$N(R^{16f})_2$, —$NO_2$, —$CF_3$, —$OCF_3$, —$SR^{16f}$, —$S(O)R^{16f}$, —$SO_2R^{16f}$, —C(O)H, —$C(O)R^{16f}$, —C(O)OH, —$C(O)OR^{16f}$, —$C(O)NH_2$, —$C(O)NHR^{16f}$, or —$C(O)N(R^{16f})_2$ substituents; $R^{16f}$ is $C_1$-alkyl, $C_2$-alkyl, $C_3$-alkyl, $C_4$-alkyl, $C_5$-alkyl, or $C_6$-alkyl; $R^{17}$ is $C_2$-alkenyl, $C_3$-alkenyl, $C_4$-alkenyl, $C_5$-alkenyl, $C_6$-alkenyl, or $R^{17a}$; $R^{17a}$ is $C_2$-alkenyl, $C_3$-alkenyl, $C_4$-alkenyl, $C_5$-alkenyl, or $C_6$-alkenyl, each of which is substituted with one or two independently selected —$CF_3$, —$CF_2CF_3$, —F, —Cl, —Br, —I, —OH, —$OR^{17b}$, —$NH_2$, —$NHR^{17b}$, —$N(R^{17b})_2$, or $R^{17c}$ substituents; $R^{17b}$ is $C_1$-alkyl, $C_2$-alkyl, $C_3$-alkyl, $C_4$-alkyl, $C_5$-alkyl, or $C_6$-alkyl; $R^{17c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{17d}$, —F, —Cl, —Br, —I, —CN, —OH, —$OR^{17d}$, —$NH_2$, —$NHR^{17d}$, —$N(R^{17d})_2$, —$NO_2$, —$CF_3$, —$OCF_3$, —$SR^{17d}$, —$S(O)R^{17d}$, —$SO_2R^{17d}$, —C(O)H, —$C(O)R^{17d}$, —C(O)OH, —$C(O)OR^{17d}$, —$C(O)NH_2$, —$C(O)NHR^{17d}$, —$C(O)N(R^{17d})_2$, or $R^{17e}$ substituents; $R^{17d}$ is $C_1$-alkyl, $C_2$-alkyl, $C_3$-alkyl, $C_4$-alkyl, $C_5$-alkyl, or $C_6$-alkyl; $R^{17e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{17f}$, —F, —Cl, —Br, —I, —CN, —OH, —$OR^{17f}$, —$NH_2$, —$NHR^{17f}$, —$N(R^{17f})_2$, —$NO_2$, —$CF_3$, —$OCF_3$, —$SR^{17f}$, —$S(O)R^{17f}$, —$SO_2R^{17f}$, —C(O)H, —$C(O)R^{17f}$, —C(O)OH, —$C(O)OR^{17f}$, —$C(O)NH_2$, —$C(O)NHR^{17f}$, or —$C(O)N(R^{17f})_2$ substituents; $R^{17f}$ is $C_1$-alkyl, $C_2$-alkyl, $C_3$-alkyl, $C_4$-alkyl, $C_5$-alkyl, or $C_6$-alkyl; $R^{18}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{18a}$, —F, —Cl, —Br, —I, —CN, —OH, —$OR^{18a}$, —$NH_2$, —$NHR^{18a}$, —$N(R^{18a})_2$, —$NO_2$, —$CF_3$, —$OCF_3$, —$SR^{18a}$, —$S(O)R^{18a}$, —$SO_2R^{18a}$, —C(O)H, —$C(O)R^{18a}$, —C(O)OH, —$C(O)OR^{18a}$, —$C(O)NH_2$, —$C(O)NHR^{18a}$, —$C(O)N(R^{18a})_2$, or $R^{18b}$ substituents; $R^{18a}$ is $C_1$-alkyl, $C_2$-alkyl, $C_3$-alkyl, $C_4$-alkyl, $C_5$-alkyl, or $C_6$-alkyl; $R^{18b}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{18c}$, —F, —Cl, —Br, —I, —CN, —OH, —$OR^{18c}$, —$NH_2$, —$NHR^{18c}$, —$N(R^{18c})_2$, —$NO_2$, —$CF_3$, —$OCF_3$, —$SR^{18c}$, —$S(O)R^{18c}$, —$SO_2R^{18c}$, —C(O)H, —$C(O)R^{18c}$, —C(O)OH, —$C(O)OR^{18c}$, —$C(O)NH_2$, —$C(O)NHR^{18c}$, or —$C(O)N(R^{18c})_2$ substituents; $R^{18c}$ is $C_1$-alkyl, $C_2$-alkyl, $C_3$-alkyl, $C_4$-alkyl, $C_5$-alkyl, or $C_6$-alkyl; $R^{19}$ is $C_1$-alkyl, $C_2$-alkyl, $C_3$-alkyl, $C_4$-alkyl, $C_5$-alkyl, $C_6$-alkyl, or $R^{19a}$; $R^{19a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^9$, —$NH_2$, —$NHR^9$, —$N(R^{19b})_2$, or $R^{19c}$ substituents; $R^{19b}$ is $C_1$-alkyl, $C_2$-alkyl, $C_3$-alkyl, $C_4$-alkyl, $C_5$-alkyl, or $C_6$-alkyl; $R^{19c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{19d}$, —F, —Cl, —Br, —I, —CN, —OH, —$OR^{19d}$, —$NH_2$, —$NHR^{19d}$, —$N(R^{19d})_2$, —$NO_2$, —$CF_3$, —$OCF_3$, —$SR^{19d}$, —$S(O)R^{19d}$, —$SO_2R^{19d}$, —C(O)H, —$C(O)R^{19d}$, —C(O)OH, —$C(O)OR^{19d}$, —$C(O)NH_2$, —$C(O)NHR^{19d}$, —$C(O)N(R^{19d})_2$, or $R^{19e}$ substituents; $R^{19d}$ is $C_1$-alkyl, $C_2$-alkyl, $C_3$-alkyl, $C_4$-alkyl, $C_5$-alkyl, or $C_6$-alkyl; $R^{19e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{19f}$, —F, —Cl, —Br, —I, —CN, —OH, —$OR^{19f}$, —$NH_2$, —$NHR^{19f}$, —$N(R^{19f})_2$, —$NO_2$, —$CF_3$, —$OCF_3$, —$SR^{19f}$, —$S(O)R^{19f}$, —$SO_2R^{19f}$, —C(O)H, —$C(O)R^{19f}$, —C(O)OH, —$C(O)OR^{19f}$, —$C(O)NH_2$, —$C(O)NHR^{19f}$, or —$C(O)N(R^{19f})_2$ substituents; $R^{19f}$ is $C_1$-alkyl, $C_2$-alkyl, $C_3$-alkyl, $C_4$-alkyl, $C_5$-alkyl, or $C_6$-alkyl; $R^{20}$ is $C_1$-alkyl, $C_2$-alkyl, $C_3$-alkyl, $C_4$-alkyl, $C_5$-alkyl, $C_6$-alkyl, or $R^{20a}$; $R^{20a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{20b}$, —$NH_2$, —$NHR^{20b}$, —$N(R^{20b})_2$, or $R^{20c}$ substituents; $R^{20b}$ is $C_1$-alkyl, $C_2$-alkyl, $C_3$-alkyl, $C_4$-alkyl, $C_5$-alkyl, or $C_6$-alkyl; $R^{20c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{20d}$, —F, —Cl, —Br, —I, —CN, —O, —$OR^{20d}$, —$NH_2$, —$NHR^{20d}$, —$N(R^{20d})_2$, —NO, —$CF_3$, —$OCF_3$, —$SR^{20d}$, —$S(O)R^{20d}$, —$SO_2R^{20d}$, —C(O)H, —$C(O)R^{20d}$, —C(O)OH, —$C(O)OR^{20d}$, —$C(O)NH_2$, —$C(O)NHR^{20d}$, —$C(O)N(R^{20d})_2$, or $R^{20e}$ substituents; $R^{20d}$ is $C_1$-alkyl, $C_2$-alkyl, $C_3$-alkyl, $C_4$-alkyl, $C_5$-alkyl, or $C_6$-alkyl; $R^{20e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{20f}$, —F, —Cl, —Br, —I, —CN, —OH, —$OR^{20f}$, —$NH_2$, —$NHR^{20f}$, —$N(R^{20f})_2$, —$NO_2$, —$CF_3$, —$OCF_3$, —$SR^{20f}$, —$S(O)R^{20f}$, —$SO_2R^{20f}$, —C(O)H, —$C(O)R^{20f}$, —C(O)OH, —$C(O)OR^{20f}$, —$C(O)NH_2$, —$C(O)NHR^{20f}$, or —$C(O)N(R^{20f})_2$ substituents; $R^{20f}$ is $C_1$-alkyl, $C_2$-alkyl, $C_3$-alkyl, $C_4$-alkyl, $C_5$-alkyl, or $C_6$-alkyl; $R^{21}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 21,2,3-triazolyl, or thiophenyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{21a}$, —F, —Cl, —Br, —I, —CN, —OH, —$OR^{21a}$, —$NH_2$, —$NHR^{21a}$, —$N(R^{21a})_2$, —$NO_2$, —$CF_3$, —$OCF_3$, —$SR^{21a}$, —$S(O)R^{21a}$, —$SO_2R^{21a}$, —$C(O)H$, —$C(O)R^{21a}$, —$C(O)OH$, —$C(O)OR^{21a}$, —$C(O)NH_2$, —$C(O)NHR^{21a}$, —$C(O)N(R^{21a})_2$, or $R^{21b}$ substituents; $R^{21a}$ is $C_1$-alkyl, $C_2$-alkyl, $C_3$-alkyl, $C_4$-alkyl, $C_5$-alkyl, or $C_6$-alkyl; $R^{21b}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 21,2,3-triazolyl, or thiophenyl, each of which is unsubstituted or substituted with one or two or three independently selected $R^{21c}$, —F, —Cl, —Br, —I, —CN, —OH, —$OR^{21c}$, —$NH_2$, —$NHR^{21c}$, —$N(R^{21c})_2$, —$NO_2$, —$CF_3$, —$OCF_3$ $SR^{21c}$, —$S(O)R^{21c}$, —$SO_2R^{21c}$, —$C(O)H$, —$C(O)R^{21c}$, —$C(O)OH$, —$C(OR^{21c}$, —$C(O)NH_2$, —$C(O)NHR^{21c}$, or —$C(O)N(R^{21c})_2$ substituents; $R^{21c}$ is —$C_1$-alkyl, $C_2$-alkyl, $C_3$-alkyl, $C_4$-alkyl, $C_5$-alkyl, or $C_6$-alkyl; $X^1$ is —O—, —S—, —S(O)—, —$SO_2$—, —NH—, or —$NR^{22}$—; $R^{22}$ is $C_1$-alkyl, $C_2$-alkyl, $C_3$-alkyl, $C_4$-alkyl, $C_5$-alkyl, $C_6$-alkyl, —$C(O)R^{23}$, —$C(O)OR^{23}$, —$CH_2R^{24}$, —$C(O)CH_2R^{24}$, or —$C(O)OCH_2R^{24}$; $R^{23}$ is $C_1$-alkyl, $C_2$-alkyl, $C_3$-alkyl, $C_4$-alkyl, $C_5$-alkyl, $C_6$-alkyl, or $R^{23a}$; $R^{23a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{23b}$, —$NH_2$, —$NHR^{23b}$, —$N(R^{23b})_2$, or $R^{23c}$ substituents; $R^{23c}$ is $C_1$-alkyl, $C_2$-alkyl, $C_3$-alkyl, $C_4$-alkyl, $C_5$-alkyl, or $C_6$-alkyl; $R^{23c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{23d}$, —F, —Cl, —Br, —I, —CN, —OH, —$OR^{23d}$, —$NH_2$, —$NHR^{23d}$, —$N(R^{23d})_2$, —$NO_2$, —$CF_3$, —$OCF_3$, —$SR^{23d}$, —$S(O)R^{23d}$, —$SO_2R^{23d}$, —$C(O)H$, —$C(O)R^{23d}$, —$C(O)OH$, —$C(O)OR^{23d}$, —$C(O)NH_2$, —$C(O)NHR^{23d}$, or —$C(O)N(R^{23d})_2$ substituents; $R^{23d}$ is $C_1$-alkyl, $C_2$-alkyl, $C_3$-alkyl, $C_4$-alkyl, $C_5$-alkyl, or $C_6$-alkyl; $R^{24}$ is $C_2$-alkenyl, $C_3$-alkenyl, $C_4$-alkenyl, $C_5$-alkenyl, $C_6$-alkenyl, $C_2$-alkynyl, $C_3$-alkynyl, $C_4$-alkynyl, $C_5$-alkynyl, $C_6$-alkynyl, or $R^{24a}$; $R^{24a}$ is $C_2$-alkenyl, $C_3$-alkenyl, $C_4$-alkenyl, $C_5$-alkenyl, $C_6$-alkenyl, $C_2$-alkynyl, $C_3$-alkynyl, $C_4$-alkynyl, $C_5$-alkynyl, or $C_6$-alkynyl, each of which is substituted with one or two independently selected —$CF_3$, —$CF_2CF_3$, —F, —Cl, —Br, —I, —OH, —$OR^{24b}$, —$NH_2$, —$NHR^{24b}$, —$N(R^{24b})_2$, or $R^{24c}$ substituents; $R^{24b}$ is $C_1$-alkyl, $C_2$-alkyl, $C_3$-alkyl, $C_4$-alkyl, $C_5$-alkyl, or $C_6$-alkyl; $R^{24c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{24d}$, —F, —Cl, —Br, —I, —CN, —OH, —$OR^{24d}$, —$NH_2$, —$NHR^{24d}$, —$N(R^{24d})_2$, —$NO_2$, —$CF_3$, —$OCF_3$, —$SR^{24d}$, —$S(O)R^{24d}$, —$SO_2R^{24d}$, —$C(O)H$, —$C(O)R^{24d}$, —$C(O)OH$, —$C(O)OR^{24d}$, —$C(O)NH_2$, —$C(O)NHR^{24d}$, or —$C(O)N(R^{24d})_2$ substituents; and $R^{24d}$ is $C_1$-alkyl, $C_2$-alkyl, $C_3$-alkyl, $C_4$-alkyl, $C_5$-alkyl, or $C_6$-alkyl.

Another embodiment of this invention pertains to processes for making the compounds of this invention having formula (I), and salts, prodrugs, and salts of prodrugs thereof.

Still another embodiment of this invention pertains to intermediates which are used in the processes for making the compounds of this invention having formula (I), and salts, prodrugs, and salts of prodrugs thereof.

Still yet another embodiment of this invention pertains to metabolites of the compounds of this invention having formula (I), and salts, prodrugs, and salts of prodrugs thereof.

Still even yet another embodiment of this invention pertains to compositions for inhibiting bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting antibacterial-resistant bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting antibacterial-resistant bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting quinolone-resistant bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting quinolone-resistant bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free, antibacterial-resistant bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free, antibacterial-resistant bacterial protein synthesis in vitro, the compositions comprising more than one compound of this invention having formula (I), or salts, prodrugs, or salts of prodrugs thereof, and an excipient.

Still even yet another embodiment of this invention pertains to compositions for inhibiting cell-free, quinolone-resistant bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free, quinolone-resistant bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting antibacterial-resistant bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting antibacterial-resistant bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting quinolone-resistant bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting quinolone-resistant bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free bacterial-growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free, antibacterial-resistant bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free, antibacterial-resistant bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free, quinolone-resistant bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free, quinolone-resistant bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting bacterial protein synthesis in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting bacterial protein synthesis in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting antibacterial-resistant bacterial protein synthesis in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting antibacterial-resistant bacterial protein synthesis in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting quinolone-resistant bacterial protein synthesis in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting quinolone-resistant bacterial protein synthesis in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting bacterial growth in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting bacterial growth in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting antibacterial-resistant bacterial growth in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting antibacterial-resistant bacterial growth in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting quinolone-resistant bacterial growth in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting quinolone-resistant bacterial growth in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for treating bacterial infections in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for treating bacterial infections in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for treating antibacterial-resistant bacterial infections in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for treating antibacterial-resistant bacterial infections in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for treating quinolone-resistant bacterial infections in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for treating quinolone-resistant bacterial infections in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to methods for inhibiting bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting antibacterial-resistant bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting antibacterial-resistant bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting quinolone-resistant bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting quinolone-resistant bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free, antibacterial-resistant bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free, antibacterial-resistant bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free, quinolone-resistant bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free, quinolone-resistant bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting antibacterial-resistant bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting antibacterial-resistant bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting quinolone-resistant bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting quinolone-resistant bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free, antibacterial-resistant bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free, antibacterial-resistant bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free, quinolone-resistant bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free, quinolone-resistant bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting bacterial protein synthesis in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting bacterial protein synthesis in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting antibacterial-resistant bacterial protein synthesis in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting antibacterial-resistant bacterial protein synthesis in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting quinolone-resistant bacterial protein synthesis in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting quinolone-resistant bacterial protein synthesis in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting bacterial growth in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting bacterial growth in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting antibacterial-resistant bacterial growth in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting antibacterial-resistant bacterial growth in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting quinolone-resistant bacterial growth in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting quinolone-resistant bacterial growth in a fish or a mammal, the methods comprising administering therapeutically effective amounts of more than one compound of this invention having formula (I), or salts, prodrugs, or salts of prodrugs thereof.

Still even yet another embodiment of this invention pertains to methods for treating bacterial infections in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for treating bacterial infections in a fish or a mammal, the methods comprising administering therapeutically effective amounts of more than one compound of this invention having formula (I), or salts, prodrugs, or salts of prodrugs thereof.

Still even yet another embodiment of this invention pertains to methods for treating antibacterial-resistant bacterial infections in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for treating antibacterial-resistant bacterial infections in a fish or a mammal, the methods comprising administering therapeutically effective amounts of more than one compound of this invention having formula (I), or salts, prodrugs, or salts of prodrugs thereof.

Still even yet another embodiment of this invention pertains to methods for treating quinolone-resistant bacterial infections in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for treating quinolone-resistant bacterial infections in a fish or a mammal, the methods comprising administering therapeutically effective amounts of more than one compound of this invention having formula

DETAILED DESCRIPTION OF THE INVENTION

The compounds of this invention are represented by fixed and variable moieties, the latter of which are represented by identifiers (capital letters with numerical and/or alphabetical superscripts) and can be specifically embodied.

It is meant to be understood that a specific embodiment of a variable moiety can be the same or different as another specific embodiment having the same identifier if the possibility of more than one specific embodiment having that identifier exists.

The term "$C_2$-alkenyl" means ethenyl (vinyl).

The term "$C_3$-alkenyl" means 1-propen-1-yl, 1-propen-2-yl (isopropenyl), and 1-propen-3-yl (allyl).

The term "$C_4$-alkenyl" means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl, and 2-methyl-2-propen-1-yl.

The term "$C_5$-alkenyl" means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-pentadien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl, and 4-penten-2-yl.

The term "$C_6$-alkenyl" means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylenepent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl, and 4-methyl-4-penten-2-yl.

The term "$C_1$-alkyl" means methyl.

The term "$C_2$-alkyl" means ethyl.

The term "$C_3$-alkyl" means prop-1-yl and prop-2-yl (isopropyl).

The term "$C_4$-alkyl" means but-1-yl, but-2-yl, 2-methylprop-1-yl, and 2-methylprop-2-yl (tert-butyl).

The term "$C_5$-alkyl" means 2,2-dimethylprop-1-yl (neopentyl), 2-methylbut-1-yl, 2-methylbut-2-yl, 3-methylbut-1-yl, 3-methylbut-2-yl, pent-1-yl, pent-2-yl, and pent-3-yl.

The term "$C_6$-alkyl" means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl, and 4-methylpent-2-yl.

The term "$C_2$-alkynyl" means ethynyl (acetylenyl).

The term "$C_3$-alkynyl" means 1-propyn-1-yl and 2-propyn-1-yl (propargyl).

The term "$C_4$-alkynyl" means 1-butyn-1-yl, 1,3-butadiyn-1-yl, 2-butyn-1-yl, 3-butyn-1-yl, and 3-butyn-2-yl.

The term "$C_5$-alkynyl" means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl, and 4-pentyn-2-yl.

The term "$C_6$-alkynyl" means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl, and 4-methyl-2-pentyn-1-yl.

Variable moieties can combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH, —$OR^9$, —$NH_2$, —$NHR^9$, or —$N(R^9)_2$; $R^2$ is hydrogen, tert-butyl, —O(allyl), (4-methoxyphenyl)methyl, or (2,4-dimethoxy-phenyl)methyl; one of $R^4$ or $R^5$ is hydrogen, $R^{10}$, —$C(O)R^{10}$, $R^{11}$, $C(O)CH_2R^{11}$, $R^{12}$, —$C(O)CH_2R^{12}$, $R^{13}$, or —$C(O)R^{13}$, and the other is together with $R^3$ and is —$CH_2CH_2$—, —$CH_2CH_2CH_2$—, or —$CH_2CH_2CH_2CH_2$—, in which the —$CH_2CH_2$—, the —$CH_2CH_2CH_2$—, and the —$CH_2CH_2CH_2CH_2$— are unsubstituted or substituted with one $R^{10}$, $R^{11}$, $R^{12}$, $R^{13}$, —F, —Cl, —Br, —I, —OH, —$OR^{10}$, =O, $N_3$, —$NH_2$, —$NHR^{10}$, —$N(R^{10})_2$, —$NHC(O)R^{10}$, —$N(R^{14})C(O)R^{10}$, —$NHSO_2R^{10}$, —$N(R^{14})SO_2R^{10}$, or —$OSO_2OR^{10}$ substituent; $R^6$ is hydrogen, $R^{15}$, —$C(O)R^{15}$, $R^{16}$, —$C(O)CH_2R^{16}$, $R^{17}$, —$C(O)CH_2R^{17}$, $R^{18}$, or —$C(O)R^{18}$; $R^7$ is hydrogen, $R^{15}$, —$C(O)R^{15}$, $R^{16}$, —$C(O)CH_2R^{16}$, $R^{17}$, —$C(O)CH_2R^{17}$, $R^{18}$, or —$C(O)R^{18}$; or $R^6$ and $R^7$ are =O; $R^8$ is hydrogen, $R^{19}$, —OH, —$OR^{19}$, —$NH_2$, —$NHR^{19}$, —$N(R^{19})_2$, —$NHC(O)R^{19}$, —$NR^{20}C(O)R^9$, —$NHC(O)OR^{19}$, —$NR^{20}C(O)OR^{19}$, —$NHSO_2R^{19}$, —$NR^{20}SO_2R^{19}$, or $R^{21}$; $R^9$ is $C_1$-alkyl, $C_2$-alkyl, $C_3$-alkyl, $C_4$-alkyl, $C_{1-5}$-alkyl, $C_6$-alkyl, or $R^{9a}$; $R^{9a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{9b}$, —$NH_2$, —$NHR^{9b}$, —$N(R^{9b})_2$, or $R^{9c}$ substituents; $R^{9b}$ is $C_1$-alkyl, $C_2$-alkyl, $C_3$-alkyl, $C_4$-alkyl, $C_5$-alkyl, or $C_6$-alkyl; $R^{9c}$ is phenyl, furanyl, or thiophenyl; $R^{10}$ is $C_1$-alkyl, $C_2$-alkyl, $C_3$-alkyl, $C_4$-alkyl, $C_5$-alkyl, $C_6$-alkyl, or $R^{10a}$; $R^{10a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{10b}$, —$NH_2$, —$NHR^{10b}$, —$N(R^{10b})_2$ or $R^{10c}$ substituents; $R^{10b}$ is $C_1$-alkyl, $C_2$-alkyl, $C_3$-alkyl, $C_4$-alkyl, $C_5$-alkyl, or $C_6$-alkyl; $R^{10c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{10d}$, —F, —Cl, —Br, —I, —CN, —OH, —$OR^{10d}$, —$NH_2$, —$NHR^{10d}$, —$N(R^{10d})_2$, —$NO_2$, —$CF_3$, —$OCF_3$, —$SR^{10d}$, —$S(O)R^{10d}$, —$SO_2R^{10d}$, —$C(O)H$, —$C(O)R^{10d}$, —$C(O)OH$, —$C(O)OR^{10}$, —$C(O)NH_2$, —$C(O)NHR^{10d}$, —$C(O)N(R^{10d})_2$, or $R^{10e}$ substituents; $R^{10d}$ is $C_1$-alkyl, $C_2$-alkyl, $C_3$-alkyl, $C_4$-alkyl, $C_5$-alkyl, or $C_6$-alkyl; $R^{10e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{10f}$, —F, —Cl, —Br, —I, —CN, —OH, —$OR^{10f}$, —$NH_2$, —$NHR^{10f}$, —$N(R^{10f})_2$, —$NO_2$, —$CF_3$, —$OCF_3$, —$SR^{10f}$, —$S(O)R^{10f}$, —$SO_2R^{10f}$, —$C(O)H$, —$C(O)R^{10f}$, —$C(O)OH$, —$C(O)OR^{10f}$, —$C(O)NH_2$, —$C(O)NHR^{10f}$, or —$C(O)N(R^{10f})_2$ substituents; $R^{10f}$ is $C_1$-alkyl, $C_2$-alkyl, $C_3$-alkyl, $C_4$-alkyl, $C_5$-alkyl, or $C_6$-alkyl; $R^{11}$ is $C_2$-alkenyl, $C_3$-alkenyl, $C_4$-alkenyl, $C_5$-alkenyl, $C_6$-alkenyl, or $R^{11a}$; $R^{11a}$ is $C_2$-alkenyl, $C_3$-alkenyl, $C_4$-alkenyl, $C_5$-alkenyl, or $C_6$-alkenyl, each of which is substituted with one or two independently selected —$CF_3$, —$CF_2CF_3$, —F, —Cl, —Br, —I, —OH, —$OR^{11b}$, —$NH_2$, —$NHR^{11b}$, —$N(R^{11b})_2$ or $R^{11c}$ substituents; $R^{11b}$ is $C_1$-alkyl, $C_2$-alkyl, $C_3$-alkyl, $C_4$-alkyl, $C_5$-alkyl, or $C_6$-alkyl; $R^{11c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{11d}$, —F, —Cl, —Br, —I, —CN, —OH, —$OR^{11d}$, —$NH_2$, —$NHR^{11d}$, —$N(R^{11d})_2$, —$NO_2$, —$CF_3$, —$OCF_3$, —$SR^{11d}$, —$S(O)R^{11d}$, —$SO_2R^{11d}$, —$C(O)H$, —$C(O)R^{11d}$, —$C(O)OH$, —$C(O)OR^{11d}$, —$C(O)NH_2$, —$C(O)NHR^{11d}$, —$C(O)N(R^{11d})_2$, or $R^{11e}$ substituents; $R^{11d}$ is $C_1$-alkyl, $C_2$-alkyl, $C_3$-alkyl, $C_4$-alkyl, $C_5$-alkyl, or $C_6$-alkyl; $R^{11e}$ is phenyl furanyl, imidazolyl, isothiazolyl, isoxazolyl, oxazolyl, pyrazolyl, pyrazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{11f}$, —F, —Cl, —Br, —I, —CN, —OH, —$OR^{11f}$, —$NH_2$, —$NHR^{11f}$, —$N(R^{11f})_2$, —$N_2$, —$CF_3$, —$OCF_3$, —$SR^{11f}$, —$S(O)R^{11f}$, —$SO_2R^{11f}$, —$C(O)H$, —$C(O)R^{11f}$, —$C(O)OH$, —$C(O)OR^{11f}$, —$C(O)NH_2$, —$C(O)NHR^{11f}$, or —$C(O)N(R^{11f})_2$ substituents; $R^{11f}$ is $C_1$-alkyl, $C_2$-alkyl, $C_3$-alkyl, $C_4$-alkyl, $C_5$-alkyl, or $C_6$-alkyl; $R^{12}$ is $C_2$-alkenyl, $C_3$-alkenyl, $C_4$-alkenyl, $C_5$-alkenyl, $C_6$-alkenyl, or $R^{12a}$; $R^{12a}$ is $C_2$-alkenyl, $C_3$-alkenyl, $C_4$-alkenyl, $C_5$-alkenyl, or $C_6$-alkenyl, each of which is substituted with one or two independently selected —$CF_3$, —$CF_2CF_3$, —F, —Cl, —Br, —I, —OH, —$OR^{12b}$, —$NH_2$, —$NHR^{12b}$, —$N(R^{12b})_2$, or $R^{12c}$ substituents; $R^{12b}$ is $C_1$-alkyl, $C_2$-alkyl, $C_3$-alkyl, $C_4$-alkyl, $C_5$-alkyl, or $C_6$-alkyl; $R^{12c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{12d}$, —F, —Cl, —Br, —I, —CN, —OH, —$OR^{12d}$, —$NH_2$, —$NHR^{12d}$, —$N(R^{12d})_2$, —$NO_2$, —$CF_3$, —$OCF_3$, —$SR^{12d}$, —$S(O)R^{12d}$, —$SO_2R^{12d}$, —$C(O)H$, —$C(O)R^{12d}$, —$C(O)OH$, —$C(O)OR^{12d}$, —$C(O)NH_2$, —$C(O)NHR^{12d}$, —$C(O)N(R^{12d})_2$, or $R^{12e}$ substituents; $R^{12d}$ is $C_1$-alkyl, $C_2$-alkyl, $C_3$-alkyl, $C_4$-alkyl, $C_5$-alkyl, or $C_6$-alkyl; $R^{12e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{12f}$, —F, —Cl, —Br, —I, —CN, —OH, —$OR^{12f}$, —$NH_2$, —$NHR^{12f}$, —$N(R^{12f})_2$, —$NO_2$, —$CF_3$, —$OCF_3$, —$SR^{12f}$, —$S(O)R^{12f}$, —$SO_2R^{12f}$, —$C(O)H$, —$C(O)R^{12f}$, —$C(O)OR^{12f}$, —$C(O)NH_2$, —$C(O)NHR^{12f}$, or —$C(O)N(R^{12f})_2$ substituents; $R^{12f}$ is $C_1$-alkyl, $C_2$-alkyl, $C_3$-alkyl, $C_4$-alkyl, $C_5$-alkyl, or $C_6$-alkyl; $R^{13}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{13a}$, —F, —Cl, —Br, —I, —CN, —OH, —OR$^{13a}$, —NH$_2$, —NHR$^{13a}$, —N(R$^{13a}$)$_2$, —NO$_2$, —CF$_3$, —OCF$_3$, —SR$^{13a}$, —S(O)R$^{13a}$, —SO$_2$R$^{13a}$, —C(O)H, —C(O)R$^{13a}$, —C(O)OH, —C(O)OR$^{13a}$, —C(O)NH$_2$, —C(O)NHR$^{13a}$, —C(O)N(R$^{13a}$)$_2$, or $R^{13b}$ substituents; $R^{13a}$ is $C_1$-alkyl, $C_2$-alkyl, $C_3$-alkyl, $C_4$-alkyl, $C_5$-alkyl, or $C_6$-alkyl; $R^{13b}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{13c}$, —F, —Cl, —Br, —I, —CN, —OH, —OR$^{13c}$, —NH$_2$, —NHR$^{13c}$, —N(R$^{13c}$)$_2$, —NO$_2$, —CF$_3$, —OCF$_3$, —SR$^{13c}$, —S(O)R$^{13c}$, —SO$_2$R$^{13c}$, —C(O)H, —C(O)R$^{13c}$, —C(O)OH, —C(O)OR$^{13c}$, —C(O)NH$_2$, —C(O)NHR$^{13c}$, or —C(O)N(R$^{13c}$)$_2$ substituents; $R^{13c}$ is $C_1$-alkyl, $C_2$-alkyl, $C_3$-alkyl, $C_4$-alkyl, $C_5$-alkyl, or $C_6$-alkyl; $R^{14}$ is $C_1$-alkyl, $C_2$-alkyl, $C_3$-alkyl, $C_4$-alkyl, $C_5$-alkyl, $C_6$-alkyl, or $R^{14a}$; $R^{14a}$ is $C_1$-alkyl, $C_2$-alkyl, $C_3$-alkyl, $C_4$-alkyl, $C_5$-alkyl, or $C_6$-alkyl, each of which is substituted with one or two independently selected —CF$_3$, —CF$_2$CF$_3$, —F, —Cl, —Br, —I, —OH, —OR$^{14b}$, —NH$_2$, —NHR$^{14b}$, —N(R$^{14b}$)$_2$, or $R^{14c}$ substituents; $R^{14b}$ is $C_1$-alkyl, $C_2$-alkyl, $C_3$-alkyl, $C_4$-alkyl, $C_5$-alkyl, or $C_6$-alkyl; $R^{14c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{14d}$, —F, —Cl, —Br, —I, —CN, —OH, OR$^{14d}$, —NH$_2$, —NHR$^{14d}$, —N(R$^{14d}$)$_2$, —NO$_2$, —CF$_3$, —OCF$_3$, —SR$^{14d}$, —S(O)R$^{14d}$, —SO$_2$R$^{14d}$, —C(O)H —C(O)R$^{14d}$, —C(O)OH, —C(O)OR$^{14d}$, —C(O)NH$_2$, —C(O)NHR$^{14d}$, —C(O)N(R$^{14d}$)$_2$, or $R^{14e}$ substituents; $R^{14d}$ is $C_1$-alkyl, $C_2$-alkyl, $C_3$-alkyl, $C_4$-alkyl, $C_5$-alkyl, or $C_6$-alkyl; $R^{14e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{14f}$, —F, —Cl, —Br, —I, —CN, —OH, —OR$^{14f}$, —NH$_2$, —NHR$^{14f}$, —N(R$^{14f}$)$_2$, —NO$_2$, —CF$_3$, —OCF$_3$, —SR$^{14f}$, —S(O)R$^{14f}$, —SO$_2$R$^{14f}$, —C(O)H, —C(O)R$^{14f}$, —C(O)OH, —C(O)OR$^{14f}$, —C(O)NH$_2$, —C(O)NHR$^{14}$, or —C(O)N(R$^{14}$)$_2$ substituents; $R^{14f}$ is $C_1$-alkyl, $C_2$-alkyl, $C_3$-alkyl, $C_4$-alkyl, $C_5$-alkyl, or $C_6$-alkyl; $R^{15}$ is $C_1$-alkyl, $C_2$-alkyl, $C_3$-alkyl, $C_4$-alkyl, $C_5$-alkyl, $C_6$-alkyl, or $R^{15a}$; $R^{15a}$ is $C_1$-alkyl, $C_2$-alkyl, $C_3$-alkyl, $C_4$-alkyl, $C_5$-alkyl, or $C_6$-alkyl, each of which is substituted with one or two independently selected —CF$_3$, —CF$_2$CF$_3$, —F, —Cl, —Br, —I, —OH, OR$^{15b}$, —NH$_2$, —NHR$^{15b}$, —N(R$^{15b}$)$_2$, or $R^{15c}$ substituents; $R^{15b}$ is $C_1$-alkyl, $C_2$-alkyl, $C_3$-alkyl, $C_4$-alkyl, $C_5$-alkyl, or $C_6$-alkyl; $R^{15c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{15d}$, —F, —Cl, —Br, —I, —CN, —OH, —OR$^{15d}$, —NH$_2$, —NHR$^{15d}$, —N(R$^{15d}$)$_2$, —NO$_2$, —CF$_3$, —OCF$_3$, —SR$^{15d}$, —S(O)R$^{15d}$, —SO$_2$R$^{15d}$, —C(O)H —C(O)R$^{15d}$, —C(O)OH, —C(O)OR$^{15d}$, —C(O)NH$_2$, —C(O)NHR$^{15d}$, —C(O)N(R$^{15d}$)$_2$, or $R^{15e}$ substituents; $R^{15d}$ is $C_1$-alkyl, $C_2$-alkyl, $C_3$-alkyl, $C_4$-alkyl, $C_5$-alkyl, or $C_6$-alkyl; $R^{15e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{15f}$, —F, —Cl, —Br, —I, —CN, —OH, —OR$^{15f}$, —NH$_2$, —NHR$^{15f}$, —N(R$^{15}$)$_2$, —NO$_2$, —CF$_3$, —OCF$_3$ —SR$^{15f}$, —S(O)R$^{15f}$, —SO$_2$R$^{15f}$, —C(O)H, —C(O)R$^{15f}$, C(O)OH, —C(O)OR$^{15f}$, —C(O)NH$_2$, —C(O)NHR$^{15f}$, or —C(O)N(R$^{15f}$)$_2$ substituents; $R^{15f}$ is $C_1$-alkyl, $C_2$-alkyl, $C_3$-alkyl, $C_4$-alkyl, $C_5$-alkyl, or $C_6$-alkyl; $R^{16}$ is $C_2$-alkenyl, $C_3$-alkenyl, $C_4$-alkenyl, $C_5$-alkenyl, $C_6$-alkenyl, or $R^{16a}$; $R^{16a}$ is $C_2$-alkenyl, $C_3$-alkenyl, $C_4$-alkenyl, $C_5$-alkenyl, or $C_6$-alkenyl, each of which is substituted with one or two independently selected —CF$_3$, —CF$_2$CF$_3$, —F, —Cl, —Br, —I, —OH, —OR$^{16b}$, —NH$_2$, —NHR$^{16b}$, —N(R$^{16b}$)$_2$, or $R^{16b}$ substituents; $R^{16b}$ is $C_1$-alkyl, $C_2$-alkyl, $C_3$-alkyl, $C_4$-alkyl, $C_5$-alkyl, or $C_6$-alkyl; $R^{16c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{16d}$, —F, —Cl, —Br, —I, —CN, —OH, —OR$^{16d}$, —NH$_2$, —NHR$^{16d}$, —N(R$^{16d}$)$_2$, —NO$_2$, —CF$_3$, —OCF$_3$, —SR$^{16d}$, —S(O)R$^{16d}$, —SO$_2$R$^{16d}$, —C(O)H, —C(O)R$^{16d}$, C(O)OH, —C(O)OR$^{16d}$, —C(O)NH$_2$, —C(O)NHR$^{16d}$, —C(O)N(R$^{16d}$)$_2$, or $R^{16e}$ substituents; $R^{16d}$ is $C_1$-alkyl, $C_2$-alkyl, $C_3$-alkyl, $C_4$-alkyl, $C_5$-alkyl, or $C_6$-alkyl; $R^{16e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{16f}$, —F, —Cl, —Br, —I, —CN, —OH, —OR$^{16f}$, —NH$_2$, —NHR$^{16f}$, —N(R$^{16f}$)$_2$, —NO$_2$, —CF$_3$, —OCF$_3$, —SR$^{16f}$, —S(O)R$^{16f}$, —SO$_2$R$^{16f}$, —C(O) H, —C(O)R$^{16f}$, —C(O)OH, C(O)OR$^{16f}$, —C(O)NH$_2$, —C(O)NHR$^{16f}$, or —C(O)N(R$^{16f}$)$_2$ substituents; $R^{16f}$ is $C_1$-alkyl, $C_2$-alkyl, $C_3$-alkyl, $C_4$-alkyl, $C_5$-alkyl, or $C_6$-alkyl; $R^{17}$ is $C_2$-alkenyl, $C_3$-alkenyl, $C_4$-alkenyl, $C_5$-alkenyl, $C_6$-alkenyl, or $R^{17a}$; $R^{17a}$ is $C_2$-alkenyl, $C_3$-alkenyl, $C_4$-alkenyl, $C_5$-alkenyl, or $C_6$-alkenyl, each of which is substituted with one or two independently selected —CF$_3$, —CF$_2$CF$_3$, —F, —Cl, —Br, —I, —OH, —OR$^{17b}$, —NH$_2$, —NHR$^{17b}$, —N(R$^{17b}$)$_2$, or $R^{17c}$ substituents; $R^{17b}$ is $C_1$-alkyl, $C_2$-alkyl, $C_3$-alkyl, $C_4$-alkyl, $C_5$-alkyl, or $C_6$-alkyl; $R^{17c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{17d}$, —F, —Cl, —Br, —I, —CN, —OH, —OR$^{17d}$, —NH$_2$, —NHR$^{17d}$, —N(R$^{17d}$)$_2$, —NO$_2$, —CF$_3$, —OCF$_3$, —SR$^{17d}$, —S(O)R$^{17d}$, —SO$_2$R$^{17d}$, —C(O)H, —C(O)R$^{17d}$, —C(O)OH, —C(O)OR$^{17d}$, —C(O)NH$_2$, —C(O)NHR$^{17d}$, —C(O)N(R$^{17d}$)$_2$, or $R^{17e}$ substituents; $R^{17d}$ is $C_1$-alkyl, $C_2$-alkyl, $C_3$-alkyl, $C_4$-alkyl, $C_5$-alkyl, or $C_6$-alkyl; $R^{17e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{17f}$, —F, —Cl, —Br, —I, —CN, —OH, —OR$^{17f}$, —NH$_2$, —NHR$^{17f}$, —N(R$^{17f}$)$_2$, —NO$_2$, —CF$_3$, —OCF$_3$, —SR$^{17f}$, —S(O)R$^{17f}$, —SO$_2$R$^{17f}$, —C(O)H, —C(O)R$^{17f}$, —C(O)OH, —C(O)OR$^{17f}$, —C(O)NH$_2$, —C(O)NHR$^{17f}$, or —C(O)N(R$^{17f}$)$_2$ substituents; $R^{17f}$ is $C_1$-alkyl, $C_2$-alkyl, $C_3$-alkyl, $C_4$-alkyl, $C_5$-alkyl, or $C_6$-alkyl; $R^{18}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{18a}$, —F, —Cl, —Br, —I, —CN, —OH, —$OR^{18a}$, —$NH_2$, —$NHR^{18a}$, —$N(R^{18a})_2$, —$NO_2$, —$CF_3$, —$OCF_3$, —$SR^{18a}$, —$S(O)R^{18a}$, —$SO_2R^{18a}$, —C(O)H, —$C(O)R^{18a}$, —C(O)OH, —$C(O)OR^{18a}$, —$C(O)NH_2$, —$C(O)NHR^{18a}$, —$C(O)N(R^{18a})_2$, or $R^{18b}$ substituents; $R^{18a}$ is $C_1$-alkyl, $C_2$-alkyl, $C_3$-alkyl, $C_4$-alkyl, $C_5$-alkyl, or $C_6$-alkyl; $R^{18b}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{18c}$, —F, —Cl, —Br, —I, —CN, —OH, —$OR^{18c}$, —$NH_2$, —$NHR^{18c}$, —$N(R^{18c})_2$, —$NO_2$, —$CF_3$, —$OCF_3$, —$SR^{18c}$, —$S(O)R^{18c}$, —$SO_2R^{18c}$, —C(O)H, —$C(O)R^{18c}$, —C(O)OH, —$C(O)OR^{18c}$, —$C(O)NH_2$, —$C(O)NHR^{18c}$, or —$C(O)N(R^{18c})_2$ substituents; $R^{18c}$ is $C_1$-alkyl, $C_2$-alkyl, $C_3$-alkyl, $C_4$-alkyl, $C_5$-alkyl, or $C_6$-alkyl; $R^{19}$ is $C_1$-alkyl, $C_2$-alkyl, $C_3$-alkyl, $C_4$-alkyl, $C_5$-alkyl, $C_6$-alkyl, or $R^{19a}$; $R^{19a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{19b}$, —$NH_2$, —$NHR^{19b}$, —$N(R^{19b})_2$, or $R^{19c}$ substituents; $R^{19b}$ is $C_1$-alkyl, $C_2$-alkyl, $C_3$-alkyl, $C_4$-alkyl, $C_5$-alkyl, or $C_6$-alkyl; $R^{19c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{19d}$, —F, —Cl, —Br, —I, —CN, —OH, —$OR^{19d}$, —$NH_2$, —$NHR^{19d}$, —$N(R^{19d})_2$, —$NO_2$, —$CF_3$, —$OCF_3$, —$SR^{19d}$, —$S(O)R^{19d}$, —$SO_2R^{19d}$, —C(O)H —$C(O)R^{19d}$, —C(O)OH, —$C(O)OR^9$, —$C(O)NH_2$, —$C(O)NHR^{19d}$, —$C(O)N(R^{19d})_2$, or $R^{19e}$ substituents; $R^{19d}$ is $C_1$-alkyl, $C_2$-alkyl, $C_3$-alkyl, $C_4$-alkyl, $C_5$-alkyl, or $C_6$-alkyl; $R^{19e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{19f}$, —F, —Cl, —Br, —I, —CN, —OH, —$OR^{19f}$, —$NH_2$, —$NHR^{19f}$, —$N(R^{19f})_2$, —$NO_2$, —$CF_3$, —$OCF_3$, —$SR^{19f}$, —$S(O)R^{19f}$, —$SO_2R^{19f}$, —C(O)H, —$C(O)R^{19f}$, —C(O)OH, —$C(O)OR^{19f}$, —$C(O)NH_2$, —$C(O)NHR^{19f}$, or —$C(O)N(R^{19f})_2$ substituents; $R^{19f}$ is $C_1$-alkyl, $C_2$-alkyl, $C_3$-alkyl, $C_4$-alkyl, $C_5$-alkyl, or $C_6$-alkyl; $R^{20}$ is $C_1$-alkyl, $C_2$-alkyl, $C_3$-alkyl, $C_4$-alkyl, $C_5$-alkyl, $C_6$-alkyl, or $R^{20a}$; $R^{20a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{20b}$, —$NH_2$, —$NHR^{20b}$, —$N(R^{20b})_2$, or $R^{20c}$ substituents; $R^{20b}$ is $C_1$-alkyl, $C_2$-alkyl, $C_3$-alkyl, $C_4$-alkyl, $C_5$-alkyl, or $C_6$-alkyl; $R^{20c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{20d}$, —F, —Cl, —Br, —I, —CN, —OH, —$OR^{20d}$, —$NH_2$, —$NHR^{20d}$, —$N(R^{20d})_2$, —$NO_2$, —$CF_3$, —$OCF_3$, —$SR^{20d}$, —$S(O)R^{20d}$, —$SO_2R^{20d}$, —C(O)H —$C(O)R^{20d}$, —C(O)OH, —$C(O)OR^{20d}$, —$C(O)NH_2$, —$C(O)NHR^{20d}$, —$C(O)N(R^{20d})_2$, or $R^{20e}$ substituents; $R^{20d}$ is $C_1$-alkyl, $C_2$-alkyl, $C_3$-alkyl, $C_4$-alkyl, $C_5$-alkyl, or $C_6$-alkyl; $R^{20e}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl ring, each of which is unsubstituted or substituted with one or two or three independently selected $R^{20f}$, —F, —Cl, —Br, —I, —CN, —OH, —$OR^{20f}$, —$NH_2$, —$NHR^{20f}$, —$N(R^{20f})_2$, —$NO_2$, —$CF_3$, —$OCF_3$, —$SR^{20f}$, —$S(O)R^{20f}$, —$SO_2R^{20f}$, —C(O)H, —$C(O)R^{20f}$, —C(O)OH, —$C(O)OR^{20f}$, —$C(O)NH_2$, —$C(O)NHR^{20f}$, or —$C(O)N(R^{20f})_2$ substituents; $R^{20f}$ is $C_1$-alkyl, $C_2$-alkyl, $C_3$-alkyl, $C_4$-alkyl, $C_5$-alkyl, or $C_6$-alkyl; $R^{21}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 21,2,3-triazolyl, or thiophenyl, each of which is unsubstituted or substituted with one or two or three independently selected $R^{21a}$, —F, —Cl, —Br, —I, —CN, —OH, —$OR^{21a}$, —$NH_2$, —$NHR^{21a}$, —$N(R^{21a})_2$, —$NO_2$, —$CF_3$, —$OCF_3$, —$SR^{21a}$, —$S(O)R^{21a}$, —$SO_2R^{21a}$—C(O)H, —$C(O)R^{21a}$, —C(O)OH, —$C(O)OR^{21a}$, —$C(O)NH_2$, —$C(O)NHR^{21a}$, —$C(O)N(R^{21a})_2$, or $R^{21b}$ substituents; $R^{21a}$ is —$C_1$-alkyl, $C_2$-alkyl, $C_3$-alkyl, $C_4$-alkyl, $C_5$-alkyl, or $C_6$-alkyl; $R^{21b}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{21c}$, —F, —Cl, —Br, —I, —CN, —OH, —$OR^{21c}$, —$NH_2$, —$NHR^{21c}$, —$N(R^{21c})_2$, —$NO_2$, —$CF_3$, —$OCF_3$, —$SR^{21c}$, —$S(O)R^{21c}$, —$SO_2R^{21c}$, —C(O)H, —$C(O)R^{21c}$, —C(O)OH, $C(O)OR^{21c}$, —$C(O)NH_2$, —$C(O)NHR^{21c}$, or —$C(O)N(R^{21c})_2$ substituents; $R^{21c}$ is —$C_1$-alkyl, $C_2$-alkyl, $C_3$-alkyl, $C_4$-alkyl, $C_5$-alkyl, or $C_6$-alkyl; $X^1$ is —O—, —S—, —S(O)—, —$SO_2$—, —NH—, or —$NR^{22}$—; $R^{22}$ is $C_1$-alkyl, $C_2$-alkyl, $C_3$-alkyl, $C_4$-alkyl, $C_5$-alkyl, $C_6$-alkyl, —$C(O)R^{23}$, —$C(O)OR^{24}$, —$CH_2R^{24}$, —$C(O)CH_2R^{24}$, or —$C(O)OCH_2R^{24}$; $R^{23}$ is $C_1$-alkyl, $C_2$-alkyl, $C_3$-alkyl, $C_4$-alkyl, $C_5$-alkyl, $C_6$-alkyl, or $R^{23a}$; $R^{23a}$ is $C_1$-alkyl, $C_2$-alkyl, $C_3$-alkyl, $C_4$-alkyl, $C_5$-alkyl, or $C_6$-alkyl, each of which is substituted with one or two independently selected —$CF_3$, —$CF_2CF_3$, —F, —Cl, —Br, —I, —OH, —$OR^{23b}$, —$NH_2$, —$NHR^{23b}$, —$N(R^{23b})_{22}$ or $R^{23c}$ substituents; $R^{23b}$ is $C_1$-alkyl, $C_2$-alkyl, $C_3$-alkyl, $C_4$-alkyl, $C_5$-alkyl, or $C_6$-alkyl; $R^{23c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{23d}$, —F, —Cl, —Br, —I, —CN, —OH, —$OR^{23d}$, —$NH_2$, —$NHR^{23d}$, —$N(R^{23d})_2$, —$NO_2$, —$CF_3$, —$OCF_3$, —$SR^{23d}$, —$S(O)R^{23d}$, —$SO_2R^{23d}$, —C(O)H, —$C(O)R^{23d}$, C(O)OH, —$C(O)OR^{23d}$, —$C(O)NH_2$, —$C(O)NHR^{23d}$, or —$C(O)N(R^{23d})_2$ substituents; $R^{23d}$ is $C_1$-alkyl, $C_2$-alkyl, $C_3$-alkyl, $C_4$-alkyl, $C_5$-alkyl, or $C_6$-alkyl; $R^{24}$ is $C_2$-alkenyl, $C_3$-alkenyl, $C_4$-alkenyl, $C_5$-alkenyl, $C_6$-alkenyl, $C_2$-alkynyl, $C_3$-alkynyl, $C_4$-alkynyl, $C_5$-alkynyl, $C_6$-alkynyl, or $R^{24a}$; $R^{24a}$ is $C_2$-alkenyl, $C_3$-alkenyl, $C_4$-alkenyl, $C_5$-alkenyl, $C_6$-alkenyl, $C_2$-alkynyl, $C_3$-alkynyl, $C_4$-alkynyl, $C_5$-alkynyl, or $C_6$-alkynyl, each of which is substituted with one or two independently selected —$CF_3$, —$CF_2CF_3$, —F, —Cl, —Br, —I, —OH, —$OR^{24b}$, —$NH_2$, —$NHR^{24b}$, —$N(R^{24b})_2$, or $R^{24c}$ substituents; $R^{24b}$ is $C_1$-alkyl, $C_2$-alkyl, $C_3$-alkyl, $C_4$-alkyl, $C_5$-alkyl, or $C_6$-alkyl; $R^{24c}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{24d}$, —F, —Cl, —Br, —I, —CN, —OH, —$OR^{24d}$, —$NH_2$, —$NHR^{24d}$, —$N(R^{24d})_2$, —$NO_2$, —$CF_3$, —$OCF_3$, —$SR^{24d}$, —$S(O)R^{24d}$, —$SO_2R^{24d}$, —C(O)H, —$C(O)R^{24d}$, —C(O)OH, —$C(O)OR^{24d}$, —$C(O)NH_2$, —$C(O)NHR^{24d}$, or —$C(O)N(R^{24d})_2$ substituents; and $R^{24d}$ is $C_1$-alkyl, $C_2$-alkyl, $C_3$-alkyl, $C_4$-alkyl, $C_5$-alkyl, or $C_6$-alkyl.

Variable moieties can combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH, —OR$^9$, —NH$_2$, —NHR$^9$, or —N(R$^9$)$_2$; $R^2$ is hydrogen, tert-butyl, —O(allyl), (4-methoxyphenyl)methyl, or (2,4-dimethoxy-phenyl)methyl; one of $R^4$ or $R^5$ is hydrogen, $R^{10}$, —C(O)R$^{10}$, $R^{11}$, —C(O)CH$_2$R$^{11}$, $R^{12}$, —C(O)CH$_2$R$^{12}$, $R^{13}$, or —C(O)R$^{13}$, and the other is together with $R^3$ and is —CH$_2$CH$_2$—, —CH$_2$CH$_2$CH$_2$—, or —CH$_2$CH$_2$CH$_2$CH$_2$—, in which the —CH$_2$CH$_2$—, the —CH$_2$CH$_2$CH$_2$—, and the —CH$_2$CH$_2$CH$_2$CH$_2$— are unsubstituted or substituted with one $R^{10}$, $R^{11}$, $R^{12}$, $R^{13}$, —F, —Cl, —Br, —I, —OH, —OR$^{10}$, =O, —N$_3$, —NH$_2$, —NHR$^{10}$(alkyl), —N(R$^{10}$)$_2$, —NHC(O)R$^{10}$, —N(R$^{14}$)C(O)R$^{10}$, —NHSO$_2$R$^{10}$, —N(R$^{14}$)SO$_2$R$^{10}$, or —OSO$_2$OR$^{10}$ substituent; $R^6$ is hydrogen, $R^{15}$, —C(O)R$^{15}$, $R^{16}$, —C(O)CH$_2$R$^{16}$, $R^{17}$, —C(O)CH$_2$R$^{17}$, $R^{18}$ or —C(O)R$^{18}$; $R^7$ is hydrogen, $R^{15}$, —C(O)R$^{15}$, $R^{16}$, —C(O)CH$_2$R$^{16}$, $R^{17}$, —C(O)CH$_2$R$^{17}$, $R^{18}$, or —C(O)R$^{18}$; or $R^6$; or $R^7$ and $R^8$ are =O; $R^{19}$ is hydrogen, $R^{19}$, —OH, —OR$^{19}$, —NH$_2$, —NHR$^{19}$, —N(R$^{19}$)$_2$, —NHC(O)R$^{19}$, —NR$^{20}$C(O)R$^{19}$, —NHC(O)OR$^{19}$, —NR$^{20}$C(O)OR$^{19}$, —NHSO$_2$R$^{19}$, —NR$^{20}$SO$_2$R$^{19}$, or $R^{21}$; $R^9$ is C$_1$-alkyl, C$_2$-alkyl, C$_3$-alkyl, C$_4$-alkyl, C$_5$-alkyl, or C$_6$-alkyl; $R^{10}$ is C$_1$-alkyl, C$_2$-alkyl, C$_3$-alkyl, C$_4$-alkyl, C$_5$-alkyl, or C$_6$-alkyl; $R^{11}$ is C$_2$-alkenyl, C$_3$-alkenyl, C$_4$-alkenyl, C$_5$-alkenyl, or C$_6$-alkenyl; $R^{12}$ is C$_2$-alkenyl, C$_3$-alkenyl, C$_4$-alkenyl, C$_5$-alkenyl, or C$_6$-alkenyl; $R^{13}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{13a}$, —F, —Cl, —Br, —I, —CN, —OH, —OR$^{13a}$, —NH$_2$, —NHR$^{13a}$, —N(R$^{13a}$)$_2$, —NO$_2$, —CF$_3$, —OCF$_3$, —SR$^{13a}$, —S(O)R$^{13a}$, —SO$_2$R$^{13a}$, —C(O)H, —C(O)OR$^{13a}$, —C(O)NH$_2$, —C(O)NHR$^{13a}$, or —C(O)N(R$^{13a}$)$_2$ substituents; $R^{13a}$ is C$_1$-alkyl, C$_2$-alkyl, C$_3$-alkyl, C$_4$-alkyl, C$_5$-alkyl, or C$_6$-alkyl; $R^{14}$ is C$_1$-alkyl, C$_2$-alkyl, C$_3$-alkyl, C$_4$-alkyl, C$_5$-alkyl, or C$_6$-alkyl; $R^{15}$ is C$_1$-alkyl, C$_2$-alkyl, C$_3$-alkyl, C$_4$-alkyl, C$_5$-alkyl, or C$_6$-alkyl; $R^{16}$ is C$_2$-alkenyl, C$_3$-alkenyl, C$_4$-alkenyl, C$_5$-alkenyl, or C$_6$-alkenyl; $R^{17}$ is C$_2$-alkenyl, C$_3$-alkenyl, C$_4$-alkenyl, C$_5$-alkenyl, or C$_6$-alkenyl; $R^{18}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 1,2,3-triazolyl, or thiophenyl, each of which is unsubstituted or substituted with one or two or three independently selected $R^{18a}$, —F, —Cl, —Br, —I, —CN, —OH, —OR$^{18a}$, —NH$_2$, —NHR$^{18a}$, —N(R$^{18a}$)$_2$, —NO$_2$, —CF$_3$, —OCF$_3$, —SR$^{18a}$, —S(O)R$^{18a}$, —SO$_2$R$^{18a}$, —C(O)H, —C(O)R$^{18a}$, —C(O)OH, —C(O)OR$^{18a}$, —C(O)NH$_2$, —C(O)NHR$^{18a}$, or —C(O)N(R$^{18a}$)$_2$ substituents; $R^{18a}$ is C$_1$-alkyl, C$_2$-alkyl, C$_3$-alkyl, C$_4$-alkyl, C$_5$-alkyl, or C$_6$-alkyl; $R^{19}$ is C$_1$-alkyl, C$_2$-alkyl, C$_3$-alkyl, C$_4$-alkyl, C$_5$-alkyl, or C$_6$-alkyl; $R^{20}$ is C$_1$-alkyl, C$_2$-alkyl, C$_3$-alkyl, C$_4$-alkyl, C$_5$-alkyl, or C$_6$-alkyl; $R^{21}$ is phenyl furanyl, imidazolyl, isothiazolyl, isoxazolyl, oxazolyl, pyrazinyl, pyrazolyl, pyridazinyl, pyridyl, pyrimidinyl, pyrrolyl, tetrazolyl, thiazolyl, 21,2,3-triazolyl, or thiophenyl, each of which is unsubstituted or substituted with one or two or three independently selected $R^{21a}$, —F, —Cl, —Br, —I, —CN, —OH, —OR$^{21a}$, —NH$_2$, —NHR$^{21a}$, —N(R$^{21a}$)$_2$, —NO$_2$ CF$_3$, —OCF$_3$, —SR$^{21a}$, —S(O)R$^{21a}$, —SO$_2$R$^{21a}$, —C(O)H, —C(O)R$^{21a}$, —C(O)OH, —C(O)OR$^{21a}$, —C(O)NH$_2$, —C(O)NHR$^{21a}$, or —C(O)N(R$^{21a}$)$_2$ substituents; $X^1$ is —O—, —S—, —S(O)—, —SO$_2$—, —NH—, or —NR$^{22}$—; $R^{22}$ is C$_1$-alkyl, C$_2$-alkyl, C$_3$-alkyl, C$_4$-alkyl, C$_5$-alkyl, C$_6$-alkyl, —C(O)R$^{23}$, —C(O)OR$^{23}$, —CH$_2$R$^{24}$, —C(O)CH$_2$R$^{24}$, or —C(O)OCH$_2$R$^{24}$; $R^{23}$ is C$_1$-alkyl, C$_2$-alkyl, C$_3$-alkyl, C$_4$-alkyl, C$_5$-alkyl, C$_6$-alkyl, or $R^{23a}$; $R^{23a}$ is C$_1$-alkyl, C$_2$-alkyl, C$_3$-alkyl, C$_4$-alkyl, C$_5$-alkyl, or C$_6$-alkyl, each of which is substituted with one or two independently selected —CF$_3$, —CF$_2$CF$_3$, —F, —Cl, —Br, —I, —OH, —OR$^{23b}$, —NH$_2$, —NHR$^{23b}$, or —N(R$^{23b}$)$_2$ substituents; $R^{23b}$ is C$_1$-alkyl, C$_2$-alkyl, C$_3$-alkyl, C$_4$-alkyl, C$_5$-alkyl, or C$_6$-alkyl; $R^{24}$ is C$_2$-alkenyl, C$_3$-alkenyl, C$_4$-alkenyl, C$_5$-alkenyl, C$_6$-alkenyl, C$_2$-alkynyl, C$_3$-alkynyl, C$_4$-alkynyl, C$_5$-alkynyl, or C$_6$-alkynyl.

Variable moieties can also combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH, —OR$^9$, —NH$_2$, —NHR$^9$, or —N(R$^9$)$_2$; $R^2$ is hydrogen, tert-butyl, —O(allyl), (4-methoxyphenyl)methyl, or (2,4-dimethoxy-phenyl)methyl; one of $R^4$ or $R^5$ is hydrogen, $R^{10}$, —C(O)R$^{10}$, $R^{11}$, —C(O)CH$_2$R$^{11}$, $R^{12}$, or —C(O)CH$_2$R$^{12}$, and the other is together with $R^3$ and is —CH$_2$CH$_2$—, —CH$_2$CH$_2$CH$_2$—, or —CH$_2$CH$_2$CH$_2$CH$_2$—, in which the —CH$_2$CH$_2$—, the —CH$_2$CH$_2$CH$_2$—, and the —CH$_2$CH$_2$CH$_2$CH$_2$— are unsubstituted or substituted with one $R^{10}$, $R^{11}$, $R^{12}$, —F, —Cl, —Br, —I, —OH, —OR$^{10}$, —N$_3$, —NH$_2$, —NHR$^{10}$—N(R$^{10}$)$_2$, —NHC(O)R$^{10}$, —N(R$^{14}$)C(O)R$^{10}$, —NHSO$_2$R$^{10}$, —N(R$^{14}$)SO$_2$R$^{10}$, or —OSO$_2$OR$^{10}$ substituent; $R^6$ is hydrogen, $R^{15}$, —C(O)R$^{15}$, $R^{16}$, —C(O)CH$_2$R$^{16}$, $R^{17}$, or —C(O)CH$_2$R$^{17}$, $R^7$ is hydrogen, $R^{15}$, —C(O)R$^{15}$, $R^{16}$, —C(O)CH$_2$R$^{16}$, $R^{17}$, or —C(O)CH$_2$R$^{17}$; or $R^6$ and $R^7$ are =O; $R^6$ is hydrogen, $R^{19}$, —OH, —OR$^{19}$, —NH$_2$, —NHR$^{19}$, —N(R$^{19}$)$_2$, NHC(O)R$^{19}$, —NR$^{20}$C(O)R$^{19}$, —NHC(O)OR$^{19}$, —NR$^{20}$C(O)OR$^{19}$, —NHSO$_2$R$^{19}$, or —NR$^{20}$SO$_2$R$^{19}$; $R^9$ is C$_1$-alkyl, C$_2$-alkyl, C$_3$-alkyl, C$_4$-alkyl, C$_5$-alkyl, or C$_6$-alkyl; $R^{10}$ is C$_1$-alkyl, C$_2$-alkyl, C$_3$-alkyl, C$_4$-alkyl, C$_5$-alkyl, or C$_6$-alkyl; $R^{11}$ is C$_2$-alkenyl, C$_3$-alkenyl, C$_4$-alkenyl, C$_5$-alkenyl, or C$_6$-alkenyl; $R^{12}$ is C$_2$-alkenyl, C$_3$-alkenyl, C$_4$-alkenyl, C$_5$-alkenyl, or C$_6$-alkenyl; $R^{14}$ is C$_1$-alkyl, C$_2$-alkyl, C$_3$-alkyl, C$_4$-alkyl, C$_5$-alkyl, or C$_6$-alkyl; $R^{15}$ is C$_1$-alkyl, C$_2$-alkyl, C$_3$-alkyl, C$_4$-alkyl, C$_5$-alkyl, or C$_6$-alkyl; $R^{16}$ is C$_2$-alkenyl, C$_3$-alkenyl, C$_4$-alkenyl, C$_5$-alkenyl, or C$_6$-alkenyl; $R^{17}$ is C$_2$-alkenyl, C$_3$-alkenyl, C$_4$-alkenyl, C$_5$-alkenyl, or C$_6$-alkenyl; $R^{19}$ is C$_1$-alkyl, C$_2$-alkyl, C$_3$-alkyl, C$_4$-alkyl, C$_5$-alkyl, or C$_6$-alkyl; $R^{20}$ is C$_1$-alkyl, C$_2$-alkyl, C$_3$-alkyl, C$_4$-alkyl, C$_5$-alkyl, or C$_6$-alkyl; $X^1$ is —O—, —S—, —S(O)—, —SO$_2$—, —NH—, or —NR$^{22}$—; $R^{22}$ is C$_1$-alkyl, C$_2$-alkyl, C$_3$-alkyl, C$_4$-alkyl, C$_5$-alkyl, C$_6$-alkyl, —C(O)R$^{23}$, —C(O)OR$^{23}$, —CH$_2$R$^{24}$, —C(O)CH$_2$R$^{24}$, or —C(O)OCH$_2$R$^{24}$; $R^{23}$ is C$_1$-alkyl, C$_2$-alkyl, C$_3$-alkyl, C$_4$-alkyl, C$_5$-alkyl, C$_6$-alkyl, or $R^{23a}$; $R^{23a}$ is C$_1$-alkyl, C$_2$-alkyl, C$_3$-alkyl, C$_4$-alkyl, C$_5$-alkyl, or C$_6$-alkyl, each of which is substituted with one or two independently selected —CF$_3$, —CF$_2$CF$_3$, —F, —Cl, —Br, —I, —OH, —OR$^{23b}$, —NH$_2$, —NHR$^{23b}$, or —N(R$^{23b}$)$_2$ substituents; $R^{23b}$ is C$_1$-alkyl, C$_2$-alkyl, C$_3$-alkyl, C$_4$-alkyl, C$_5$-alkyl, or C$_6$-alkyl; $R^{24}$ is C$_2$-alkenyl, C$_3$-alkenyl, C$_4$-alkenyl, C$_5$-alkenyl, C$_6$-alkenyl, C$_2$-alkynyl, C$_3$-alkynyl, C$_4$-alkynyl, C$_5$-alkynyl, or C$_6$-alkynyl.

Variable moieties can combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH, —OR$^9$, or —NH$_2$; $R^2$ is hydrogen or (2,4-dimethoxyphenyl)methyl; one of $R^4$ or $R^5$ is hydrogen and the other is together with $R^3$ and is —CH$_2$CH$_2$—, —CH$_2$CH$_2$CH$_2$—, or —CH$_2$CH$_2$CH$_2$CH$_2$—, in which the —CH$_2$CH$_2$—, the —CH$_2$CH$_2$CH$_2$—, and the —CH$_2$CH$_2$CH$_2$CH$_2$— are unsubstituted or substituted with one —F, —Cl, —Br, —OH, —OR$^{10}$, =O, or —NH$_2$, substituent; R$^6$ and R$^7$ are hydrogen; R$^8$ is hydrogen, C$_1$-alkyl, C$_2$-alkyl, C$_3$-alkyl, C$_4$-alkyl, C$_5$-alkyl, or C$_6$-alkyl; R$^9$ is C$_1$-alkyl, C$_2$-alkyl, C$_3$-alkyl, C$_4$-alkyl, C$_5$-alkyl, or C$_6$-alkyl; R$^{10}$ is C$_1$-alkyl, C$_2$-alkyl, C$_3$-alkyl, C$_4$-alkyl, C$_5$-alkyl, or C$_6$-alkyl; X$^1$ is —O—, —S—, —S(O)—, —SO$_2$—, —NH—, or —NR$^{22}$—; and R$^{22}$ is C$_1$-alkyl, C$_2$-alkyl, C$_3$-alkyl, C$_4$-alkyl, C$_5$-alkyl, C$_6$-alkyl.

Variable moieties can combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which R$^1$ is —OH, —OH, —OR$^9$, or —NH$_2$; R$^2$ is hydrogen or (2,4-dimethoxy-phenyl)methyl; one of R$^4$ or R$^5$ is hydrogen and the other is together with R$^3$ and is —CH$_2$CH$_2$—, —CH$_2$CH$_2$CH$_2$—, or —CH$_2$CH$_2$CH$_2$CH$_2$—, in which the —CH$_2$CH$_2$—, the —CH$_2$CH$_2$CH$_2$—, and the —CH$_2$CH$_2$CH$_2$CH$_2$—, are unsubstituted or substituted with one —F, —Cl, —Br, —OH, —OR$^{10}$, =O, or —NH$_2$, substituent; R$^6$ and R$^7$ are hydrogen; R$^8$ is hydrogen, C$_1$-alkyl, C$_2$-alkyl, C$_3$-alkyl, C$_4$-alkyl, C$_5$-alkyl, or C$_6$-alkyl; R$^9$ is C$_1$-alkyl, C$_2$-alkyl, C$_3$-alkyl, C$_4$-alkyl, C$_5$-alkyl, or C$_6$-alkyl; R$^{10}$ is C$_1$-alkyl, C$_2$-alkyl, C$_3$-alkyl, C$_4$-alkyl, C$_5$-alkyl, or C$_6$-alkyl; X$^1$ is —O—, —S—, —S(O)—, —SO$_2$—, —NH—, or —NR$^{22}$—; and R$^{22}$ is C$_1$-alkyl, C$_2$-alkyl, C$_3$-alkyl, C$_4$-alkyl, C$_5$-alkyl, C$_6$-alkyl.

Variable moieties can combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which R$^1$ is —OH; R$^2$ is hydrogen or (2,4-dimethoxyphenyl)methyl; one of R$^4$ or R$^5$ is hydrogen and the other is together with R$^3$ and is —CH$_2$CH$_2$—, —CH$_2$CH$_2$CH$_2$—, or —CH$_2$CH$_2$CH$_2$CH$_2$—, in which the —CH$_2$CH$_2$—, the —CH$_2$CH$_2$CH$_2$—, and the —CH$_2$CH$_2$CH$_2$CH$_2$— are unsubstituted or substituted with one —OH substituent; R$^6$ and R$^7$ are hydrogen; R$^8$ is hydrogen or C$_1$-alkyl; X$^1$ is —O—, —NH—, or —NR$^{22}$—; and R$^{22}$ is C$_1$-alkyl.

R$^1$ is specifically embodied by —OH and —O(ethyl).

R$^2$ is specifically embodied by hydrogen and (2,4-dimethoxyphenyl)-methyl.

R$^3$ and R$^4$ together are specifically embodied by —CH$_2$CH$_2$—, —CH$_2$CH$_2$CH$_2$—, and —CH$_2$CH$_2$CH$_2$CH$_2$— when R$^5$ is hydrogen.

R$^3$ and R$^4$ together are specifically embodied by —CH$_2$CH$_2$CH$_2$— and —CH$_2$CH$_2$CH$_2$CH$_2$— when R$^5$ is hydrogen.

R$^6$ is embodied by hydrogen.

R$^7$ is embodied by hydrogen.

R$^8$ is embodied by hydrogen and methyl.

These specific embodiments can combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which R$^1$ is —OH or —O(ethyl); R$^2$ is hydrogen or (2,4-dimethoxyphenyl)methyl; R$^3$ and R$^4$ are propylene, ethylene, butylene, or 2-hydroxypropylene, and R$^5$ is hydrogen, or R$^3$ and R$^5$ are propylene or butylene, and R$^4$ is hydrogen; X$^1$ is —O—, —NH, or —N(methyl)-; R$^6$ is hydrogen; R$^7$ is hydrogen; and R$^8$ is hydrogen or methyl.

These specific embodiments can combine with the parent molecular moieties of the compounds of this invention to provide still even yet another embodiment of this invention, which embodiment pertains to compounds of this invention having formula (I), and salts, prodrugs, salts of prodrugs, and metabolites thereof, which compounds are (3aS)-7-oxo-2,3,3a,4,7,10-hexahydro-1H-pyrrolo[1',2':4,5]-[1,4]oxazino[3,2-b][1,8]naphthyridine-8-carboxylic acid, (3aR)-7-oxo-2,3,3a,4,7,10-hexahydro-1H-pyrrolo[1',2':4,5]-[1,4]oxazino[3,2-b][1,8]naphthyridine-8-carboxylic acid, (3aS)-6-methyl-7-oxo-2,3,3a,4,7,10-hexahydro-1H-pyrrolo[1',2':4,5][1,4]oxazino[3,2-b][1,8]naphthyridine-8-carboxylic acid, (2aS)-6-oxo-1,2,2a,3,6,9-hexahydroazeto[1',2':4,5]-[1,4]-oxazino[3,2-b][1,8]naphthyridine-7-carboxylic acid, 8-oxo-1,2,3,4,4a,5,8,11-octahydropyrido-[1',2':4,5]-[1,4]oxazino[3,2-b][1,8]naphthyridine-8-carboxylic acid, (2R,3aS)-2-hydroxy-7-oxo-2,3,3a,4,7,10-hexahydro-1H-pyrrolo[1',2':4,5][1,4]oxazino[3,2-b][1,8]naphthyridine-8-carboxylic acid, (3aS)-7-oxo-1,2,3,3a,4,5,7,10-octahydropyrrolo-[2',1':6,1]pyrazino[2,3-b][1,8]naphthyridine-8-carboxylic acid, and (3aS)5-methyl-7-oxo-1,2,3,3a,4,5,7,10-octahydropyrrolo-[2',1':6,1]pyrazino[2,3-b][1,8]naphthyridine-8-carboxylic acid.

The compounds of this invention can have one or more than one asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds of this invention having asymmetrically substituted carbon atoms enriched with one configuration over the other can be assigned the configuration which is present in the higher amount, preferably about 85% to about 95% enrichment, more preferably about 95% to about 99% enrichment, and still more preferably greater than about 99% enrichment. Accordingly, compounds of this invention can exist as enantiomers, mixtures of enantiomers, diastereomers having relative stereochemistry, diastereomers having absolute stereochemistry, diastereomers having at least one asymmetrically substituted carbon atom which is enriched in one configuration and at least one asymmetrically substituted carbon atom which is not enriched, and mixtures comprising the foregoing.

The compounds of this invention can also contain carbon-carbon double bonds or carbon-nitrogen double bonds in the Z or E configuration, in which the term "Z" means the two larger substituents are on the same side of the carbon-carbon or carbon-nitrogen double bond, and the term "E" means the two larger substituents are on opposite sides of the carbon-carbon or carbon-nitrogen double bond. The compounds of this invention can also exist as a mixture containing carbon-carbon double bonds or carbon-nitrogen double bonds in both Z and E configurations.

Prodrugs of the compounds of this invention having formula (I) are derivatives of the same which can hydrolyze, oxidize, reduce, or otherwise react under in vivo or in vitro biological conditions. Compounds of this invention having formula (I) having an —OH, —NH—, —SH, or —CO$_2$H moiety can have attached therethrough a prodrug-forming moiety which is removed by metabolic processes to release the compounds of this invention having formula (I) having the freed —OH, —NH—, —SH, or —CO$_2$H moiety in vivo. Prodrugs are useful for adjusting such pharmacokinetic properties of the compounds of this invention having formula (I), or the salts thereof, as solubility, hydrophobicity, absorption in the gastrointestinal tract, bioavailability, tissue penetration, and rate of clearance. Accordingly, still even yet another embodiment of this invention pertains to compounds of this invention having formula (I), or salts thereof, which exist as prodrugs or to which are attached prodrug-forming moieties.

Compounds of this invention having formula (I), and prodrugs thereof, can exist as acid addition salts, basic addition salts, or zwitterions. Salts of the compounds of this invention having formula (I), and prodrugs thereof, can be prepared during their isolation or following their purification. Acid addition salts of the compounds of this invention having formula (I), and prodrugs thereof, are those derived from reacting the same and an acid. For example, the acetate, adipate, alginate, bicarbonate, citrate, aspartate, benzoate, benzenesulfonate, bisulfate, butyrate, camphorate, camphorsufonate, citrate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate, and undecanoate salts of the compounds of this invention having formula (I), and prodrugs thereof, are meant to be included in this invention. Basic addition salts of the compounds of this invention having formula (I), and prodrugs thereof, can be prepared by reacting the same and a base such as the hydroxide, carbonate, bicarbonate, phosphate, hydrogen phosphate, or dihydrogen phosphate of cations such as calcium, iron, lithium, potassium, sodium, or magnesium.

Compounds of this invention having formula (I), and salts, prodrugs, and salts of prodrugs thereof, can be administered with or without an excipient. Excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof. Excipients for orally administered compounds of this invention having formula (I) and salts, prodrugs, and salts of prodrugs thereof, in solid dosage forms include agar, alginic acid, aluminum hydroxide, benzyl alcohol, benzyl benzoate, 1,3-butyleneglycol, castor oil, cellulose, cellulose acetate, cocoa butter, corn starch, corn oil, cottonseed oil, ethanol, ethyl acetate, ethyl carbonate, ethyl cellulose, ethyl laureate, ethyl oleate, gelatin, germ oil, glucose, glycerol, groundnut oil, isopropanol, isotonic saline, lactose, magnesium hydroxide, magnesium stearate, malt, olive oil, peanut oil, potassium phosphate salts, potato starch, propylene glycol, Ringer's solution, talc, tragacanth, water, safflower oil, sesame oil, sodium carboxymethyl cellulose, sodium lauryl sulfate, sodium phosphate salts, soybean oil, sucrose, tetrahydrofurfuryl alcohol, and mixtures thereof. Excipients for ophthalmically and orally administered compounds of this invention having formula (I), and salts, prodrugs, and salts of prodrugs thereof, in liquid dosage forms include benzyl alcohol, benzyl benzoate, 1,3-butyleneglycol, castor oil, corn oil, cottonseed oil, ethanol, ethyl acetate, ethyl carbonate, fatty acid esters of sorbitan, germ oil, groundnut oil, glycerol, isopropanol, olive oil, polyethylene glycols, propylene glycol, sesame oil, tetrahydrofurfuryl alcohol, water, and mixtures thereof. Excipients for osmotically administered compounds of this invention having formula (I), and salts, prodrugs, and salts of prodrugs thereof, include chlorofluoro-hydrocarbons, ethanol, isopropanol, water, and mixtures thereof. Excipients for parenterally administered compounds of this invention having formula (I), and salts, prodrugs, and salts of prodrugs thereof, include 1,3-butanediol, castor oil, corn oil, cottonseed oil, germ oil, groundnut oil, liposomes, oleic acid, olive oil, peanut oil, Ringer's solution, safflower oil, sesame oil, soybean oil, U.S.P. or isotonic sodium chloride solution, water, and mixtures thereof. Excipients for rectally and vaginally administered compounds of this invention having formula (I), and salts, prodrugs, and salts of prodrugs thereof, include cocoa butter, polyethylene glycol, wax, and mixtures thereof.

Compounds of this invention having formula (I), and salts, prodrugs, and salts of prodrugs thereof, can be administered orally, ophthalmically, osmotically, parenterally (subcutaneously, intramuscularly, intrasternally, intravenously), rectally, topically, transdermally, or vaginally. Orally administered compounds of this invention having formula (I), and salts, prodrugs, and salts of prodrugs thereof, in solid dosage forms can be administered as capsules, dragees, granules, pills, powders, and tablets. Ophthalmically and orally administered compounds of this invention having formula (I), and salts, prodrugs, or salts of prodrugs thereof, in liquid dosage forms can be administered as elixirs, emulsions, microemulsions, solutions, suspensions, and syrups. Osmotically and topically administered compounds of this invention having formula (I), and salts, prodrugs, or salts of prodrugs thereof, can be administered as creams, gels, inhalants, lotions, ointments, pastes, powders, solutions, and sprays. Parenterally administered compounds of this invention having formula (I), and salts, prodrugs, and salts of prodrugs thereof, can be administered as aqueous or oleaginous solutions or aqueous or oleaginous suspensions which comprise crystalline, amorphous, or otherwise insoluble forms of the compounds of this invention having formula (I). Rectally and vaginally administered compounds of this invention having formula (I), and salts, prodrugs, and salts of prodrugs thereof, can be administered as creams, gels, lotions, ointments, and pastes.

The therapeutically acceptable amount of a compound of this invention having formula (I), or a salt, prodrug, or salt of a prodrug thereof, depends on variables such as the recipient of treatment, the disorder being treated and the severity thereof, the composition containing the compound, the time of administration, the route of administration, the duration of treatment, the potency of the compound, the rate of clearance of the compound, and whether or not another drug is co-administered. The daily amount of a compound of this invention having formula (I), or a salt, prodrug, or salt of a prodrug thereof, administered to a patient in a single dose or in divided doses, is from about 0.1 to about 200 mg/kg body weight, preferably from about 0.25 to about 100 mg/kg body weight. Single dose compositions contain these amounts of a compound of this invention having formula (I), or a salt, prodrug, or salt of a prodrug thereof, or combinations of submultiples thereof.

To determine the antibacterial activity of the compounds of this invention having formula (I), twelve petri dishes, each containing successive aqueous dilutions of representative compounds of this invention having formula (I) in sterilized Brain Heart Infusion agar (Difco 0418-01-5) (10 mL), were inoculated with 1:100 dilutions of the representative microorganisms in TABLE 1 using a Steers replicator block (or 1:10 dilutions for slow-growing *Streptococcus* strains), co-incubated at 35-37° C. for 20-24 hours with a control plate having no compound, and inspected visually to provide the minimum inhibitory concentration (MIC), in µg/mL, by which is meant the lowest concentration of the test compound of this invention having formula (I) which yielded no growth, a slight haze, or sparsely isolated colonies on the inoculums spot as compared to growth in the control plate.

TABLE 1

| Microorganism | Code |
|---|---|
| Quinolone Succeptable *Streptococcus pneumoniae* ATCC 6303 | AA |
| Quinolone-Resistant *Streptococcus pneumoniae* 7257 | BB |

TABLE 2

| Example | AA MIC | BB MIC |
|---|---|---|
| Ciprofloxacin | 1 | 16 |
| Norfloxacin | 1 | 32 |
| Trovafloxacin | 0.06 | 4 |
| Linezolid | 2 | 0.5 |

The antibacterial activity of the representative compounds of this invention having formula (I) was superior to the control containing no compound and in the range of about 4 µg/mL to about greater than 64 µg/mL against AA and about 0.5 µg/mL to about 16 µg/mL against BB. These data demonstrate the utility of the compounds of this invention having formula (I) as antibacterials.

Bacterial protein synthesis inhibitory activity of representative compounds of this invention having formula (I) and the commercially-available antibacterials in TABLE 2 was determined by translation assays using the firefly luciferase reporter system described by Murray et al., (2001), "*Staphylococcus aureus* Cell Extract Transcription-Translation Assay: Firefly Luciferase Reporter System for Evaluating Protein Translation Inhibitors," Antimicrob. Agents Chemother. 45(6): 1900-1904, but replacing the *Staphylococcus aureus* S30 extract described therein with S30 *Streptococcus pneumoniae* extract from quinolone-succeptable *Streptococcus pneumoniae* ATCC 46919, and replacing plasmid coding for the luciferase gene with mRNA (encoding produced by in vitro transcription from the plasmid pAS10rbs3) which encoded the luciferase gene with an upstream *Streptococcus pneumoniae* promoter and Shine-Dalgarno site.

The $IC_{50}$'s of the representative compounds of this invention having formula (I), defined as concentrations of the same which caused 50% inhibition of bacterial protein synthesis, were in the range of about 1 µM to about 64 µM.

The $IC_{50}$'s of the commercially-available quinolones tested were greater than about 100 µM compared to the $IC_{50}$ of linezolid which is about 3 µM.

These data demonstrate that the commercially-available quinolones which were tested do not inhibit bacterial protein synthesis in *Streptococcus pneumoniae*, even at high concentrations, that the utility of the compounds of this invention having formula (I) as antibacterials is due, at least in part, to their ability to inhibit bacterial protein synthesis, and therefore bacterial growth, and that the inhibition of bacterial protein synthesis by the compounds of this invention having formula (I) would be comparable to the inhibition of bacterial protein synthesis provided by linezolid.

Therefore, while not being limited by theory, the compounds of this invention having formula (I) would be expected to function by a mechanism more similar to linezolid (which inhibits bacterial protein synthesis) than quinolones (which inhibit the enzyme DNA gyrase).

Because the representative compounds of this invention having formula (I) inhibit the growth of quinolone resistant bacteria at least as well as the growth of quinolone susceptible bacteria, and because they function by a mechanism which differs from quinolones, the compounds of this invention having formula (I), and the salts, prodrugs, salts of prodrugs, and metabolites thereof, would be expected to be useful not only for treating bacterial infections but also for treating bacterial infections for which quinolones would be ineffective or only partially effective.

Metabolites of the compounds of this invention having formula (I), produced by in vitro or in vivo metabolic processes, can also be useful as antibacterials. Once identified, these metabolites can also be synthesized and evaluated for utility as antibacterials.

Compounds of this invention having formula (I), and salts, prodrugs, and salts of prodrugs, can be prepared by chemical processes, examples of which chemical processes and intermediates used in the processes are shown in the following schemes. It is meant to be understood that the order of the steps in the processes can be varied, that different intermediates, reagents, solvents, and reaction conditions can be substituted for those specifically mentioned, and that vulnerable moieties can be protected and deprotected, as needed, during the processes.

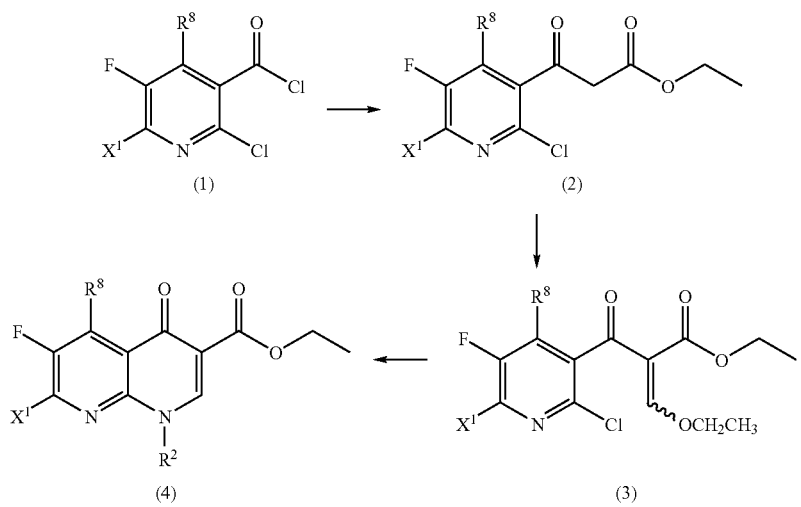

SCHEME 1

Compounds having formula (1), in which $X^1$ is —Br or —Cl, can be converted to compounds having formula (2) by reacting the former and a compound having formula (i)

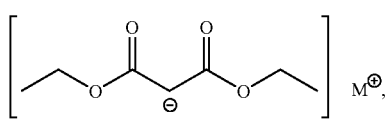
(i)

in which M is sodium or potassium. This step is typically conducted at about 0° C. to 25° C., over about 1 to 24 hours, in solvents such as dichloromethane, chloroform, THF, and mixtures thereof.

Compounds having formula (2) may be converted to compounds having formula (3) by reacting the former, triethyl orthoformate, and acetic anhydride. The reaction is typically conducted from about 1 to 6 hours, at about 80° C. to 140° C., in acetic anhydride.

Compounds having formula (3) may be converted to compounds having formula (4) by reacting the former, a first base and compounds having formula (ii)

(ii), in which $R^2$ is a nitrogen protecting group. Nitrogen protecting groups include allyloxy, 2,4-dimethoxybenzyl, 2-cyanoethyl, 4-methoxybenzyl, trimethylsilyl, tert-butyl, and triphenylmethyl. First bases include potassium carbonate, sodium carbonate, sodium hydride, and potassium hydride. The reaction is typically conducted from about ½ hour to 7 days, at about 0° C. to 100° C., in solvents such as dichloromethane, acetonitrile, THF, and mixtures thereof.

Compounds having formula (4) may be converted to compounds having formula (4a) by reacting the former and lithium hydroxide. Compounds having formula (4a) may be converted to compounds having formula (5) by reacting the former, diisopropylethylamine, and compounds having formula (iii)

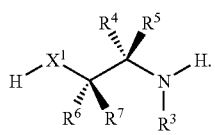
(iii)

These steps are typically conducted at about 24° C. to 40° C., over about 24 hours to 5 days, in solvents such as water, acetonitrile N,N-dimethylfromamide, dimethylsulfoxide, tetrahydrofuran, and mixtures thereof.

Compounds having formula (5) may be converted to compounds having formula (I) by reacting the former with or without the first base, depending on the nature of $X^1$.

The —$CO_2H$ moieties of the compounds of the invention can be reacted with ammonia or an amine having formula —$NHR^9$, or —$N(R^9)_2$ and a dehydrating agent, with or without the first base, and with or without a promoter. Examples of dehydrating agents include carbonyldiimidazole, 1-(3-(dimethylamino)propyl)-3-ethylcarbodiimide hydrochloride and dicyclohexylcarbodiimide. Examples of promoters include 1-hydroxybenzotriazole and 4-(N,N-dimethylamino)pyridine. The reactions are typically conducted at about 0° C. to about 35° C., for about 1 hour to about 24 hours, in solvents such as N,N-dimethylformamide, tetrahydrofuran, dioxane, water, ethyl acetate, and acetonitrile.

EXAMPLE 1A ethyl(2E/Z)-2-((2,6-dichloro-5-fluoropyridin-3-yl)carbonyl)-3-(ethoxy)prop-2-enoate A mixture of ethyl 3-(2,6-dichloro-5-fluoropyridin-3-yl)-3-oxopropanoate (40 g), triethylorthoformate (26.1 mL), and acetic anhydride (100 mL) was stirred at 85° C. for 6.5 hours, cooled, and concentrated. The concentrate was crystallized from hexanes with a small amount of diethyl ether and dichloromethane.

EXAMPLE 1B ethyl 7-chloro-1-(2,4-dimethoxybenzyl)-6-fluoro-4-oxo-1,4-dihydro[1,8]naphthyridine-3-carboxylate Example 1A in acetonitrile at 0° C. was treated with 2,4-dimethoxybenzylamine, stirred for 15 minutes, warmed to ambient temperature, stirred for 30 minutes, treated with potassium carbonate, heated at 75° C. for 18 hours, cooled, treated with ethyl acetate, washed with water, 10% citric acid, water, and brine, dried over anhydrous magnesium sulfate, filtered, and concentrated. The concentrate was plug filtered through silica gel with 9:1 ethyl acetate/dichloromethane.

EXAMPLE 1C ethyl 1-(2,4-dimethoxybenzyl)-7-(2-(S)-hydroxymethyl-pyrrolidin-1-yl)-4-oxo-1,4-dihydro-[1,8]naphthyridine-3-carboxylate A mixture of EXAMPLE 1B (2.96 g), (S)-prolinol (850 µL), and diisopropylethylamine (4 mL) in acetonitrile (70

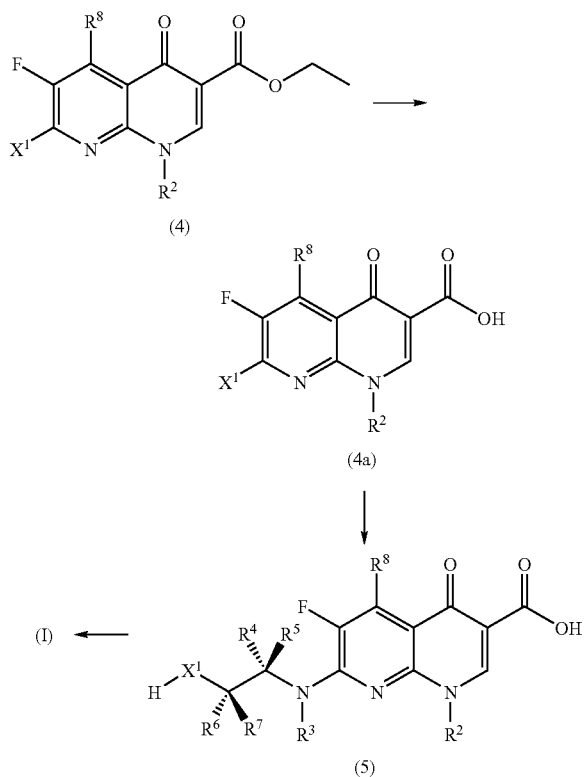

EXAMPLE 1D 1-(2,4-dimethoxybenzyl)-7-(2-(S)-hydroxymethyl-pyrrolidin-1-yl)-4-oxo-1,4-dihydro-[1,8]naphthyridine-3-carboxylic acid A mixture of EXAMPLE 1C (2 g) and 0.1M lithium hydroxide (80 mL) in ethanol (100 mL) at 25° C. was stirred for 24 hours, adjusted to pH 3 with 1M hydrochloric acid, treated with water, and filtered.

EXAMPLE 1E (3aS)-10-(2,4-dimethoxybenzyl)-7-oxo-2,3,3a,4,7,10-hexahydro-1H-pyrrolo[1',2':4,5][1,4]oxazino[3,2-b][1,8]-naphthyridine-8-carboxylic acid EXAMPLE 1D (1.48 g) in N,N-dimethylformamide (75 mL) at 0° C. was treated with 60% oily sodium hydride (330 mg), stirred for 30 minutes, heated at 90-115° C. for 34 hours, cooled, treated with water, adjusted to pH 3 with 1M hydrochloric acid, and filtered.

EXAMPLE 1F (3aS)-7-oxo-2,3,3a,4,7,10-hexahydro-1H-pyrrolo[1',2':4,5]-[1,4]oxazino[3,2-b][1,8]naphthyridine-8-carboxylic acid EXAMPLE 1E (251 mg) in trifluoroacetic acid (12 mL) at 70° C. was stirred for 3 hours, cooled, and concentrated with a toluene azeotrope. The concentrate was dissolved in acetonitrile (20 mL), and this solution was treated with water and filtered. The filtrant was purified by flash column chromatography on silica gel with 9:1 dichloromethane/methanol. $^1$H NMR (500 MHz, DMSO-$d_6$) δ 15.7 (br s, 1H), 12.8 (br s, 1H), 8.3 (s, 1H), 7.5 (s, 1H), 4.62 (dd, J=10.99 Hz, 3.66 Hz, 1H), 3.8 (m, 1H), 3.7-3.6 (m, 2H), 3.6 (m, 1H), 2.2 (m, 1H), 2.1 (m, 1H), 2.0 (m, 1H), 1.56 (m, 1H).

EXAMPLE 2A ethyl 1-(2,4-dimethoxybenzyl)-7-(2-(R)-hydroxymethyl-pyrrolidin-1-yl)-4-oxo-1,4-dihydro-[1,8]naphthyridine-3-carboxylate A mixture of EXAMPLE 1B (2.96 g), (R)-prolinol (850 µL) and diisopropylethylamine (4 mL) in acetonitrile (70 mL) at 25° C. was stirred for 3 days, treated with water, and filtered.

EXAMPLE 2B 1-(2,4-dimethoxy-benzyl)-7-(2-(R)-hydroxymethyl-pyrrolidin-1-yl)-4-oxo-1,4-dihydro-[1,8]naphthyridine-3-carboxylic acid A mixture of EXAMPLE 2A (2 g) and 0.1M lithium hydroxide (80 mL) in ethanol (100 mL) at 25° C. was stirred for 24 hours, adjusted to pH 3 with 1M hydrochloric acid, treated with water, and filtered.

EXAMPLE 2C (3aR)-10-(2,4-dimethoxybenzyl)-7-oxo-2,3,3a,4,7,10-hexahydro-1H-pyrrolo[1',2':4,5][1,4]oxazino[3,2-b][1,8]-naphthyridine-8-carboxylic acid EXAMPLE 2B (1.51 g) in N,N-dimethylformamide (75 mL) at 0° C. was treated with 60% oily sodium hydride (330 mg), stirred for 30 minutes, heated at 90-115° C. for 34 hours, cooled, treated with water, adjusted to pH 3 with 1M hydrochloric acid, and filtered.

EXAMPLE 2D (3aR)-7-oxo-2,3,3a,4,7,10-hexahydro-1H-pyrrolo[1',2':4,5]-[1,4]oxazino[3,2-b][1,8]naphthyridine-8-carboxylic acid EXAMPLE 2C (252 mg) in trifluoroacetic acid (15 mL) at 70° C. was stirred for 3 hours, cooled, and concentrated with a toluene azeotrope. The concentrate was dissolved in acetonitrile (20 mL), and this solution was treated with water, filtered, and flash chromatographed on silica gel with 9:1 dichloromethane/methanol. $^1$H NMR (500 MHz, DMSO-$d_6$) δ 15.7 (br s, 1H), 8.35 (s, 1H), 7.5 (s, 1H), 4.6 (m, 1H), 3.8 (m, 1H), 3.7-3.5 (m, 3H), 2.2 (m, 1H), 2.1 (m, 1H), 2.0 (m, 1H), 1.6 (m, 1H).

EXAMPLE 3A ethyl 1-(2,4-dimethoxybenzyl)-6-fluoro-7-((2S)-2-(hydroxymethyl)pyrrolidinyl)-5-methyl-4-oxo-1,4-dihydro-[1,8]naphthyridine-3-carboxylate This example was prepared by substituting ethyl 7-chloro-1-(2,4-dimethoxybenzyl)-6-fluoro-5-methyl-4-oxo-1,4-dihydro[1,8]naphthyridine-3-carboxylate for EXAMPLE 1B in EXAMPLE 1C.

EXAMPLE 3B 1-(2,4-dimethoxybenzyl)-6-fluoro-7-((2S)-2-(hydroxymethyl)-pyrrolidinyl)-5-methyl-4-oxo-1,4-dihydro[1,8]naphthyridine-3-carboxylic acid A mixture of EXAMPLE 3A (312 mg) and 1M lithium hydroxide (1.9 mL) in methanol (6 mL) at 25° C. was stirred for 24 hours, treated with water (100 mL), adjusted to pH 3 with 1M hydrochloric acid, and filtered.

EXAMPLE 3C (3aS)-10-(2,4-dimethoxybenzyl)-6-methyl-7-oxo-2,3,3a,4,7,10-hexahydro-1H-pyrrolo[1',2':4,5]-[1,4]oxazino[3,2-b][1,8]naphthyridine-8-carboxylic acid EXAMPLE 3B (311 mg) in N,N-dimethylformamide (16 mL) at 0° C. was treated with 60% oily sodium hydride (71 mg), stirred for 30 minutes, heated at 110° C. for 3 days and cooled, treated with 60% oily sodium hydride (36 mg), heated at 110° C. for 5 days and cooled, treated with 60% oily sodium hydride (69 mg), heated at 110° C. for 2 days and cooled, treated with water, adjusted to pH 3 with 1M hydrochloric acid, and filtered.

EXAMPLE 3D (3aS)-6-methyl-7-oxo-2,3,3a,4,7,10-hexahydro-1H-pyrrolo[1',2':4,5][1,4]oxazino[3,2-b][1,8]naphthyridine-8-carboxylic acid EXAMPLE 3C (286 mg) in trifluoroacetic acid (10 mL) at 70° C. was stirred for 4 hours, cooled, and concentrated. The concentrate was azeotroped with toluene and crystallized from dimethylsulfoxide. $^1$H NMR (300 MHz, DMSO-$d_6$) δ 12.92 (m, 1H), 8.30 (m, 1H), 4.68 (dd, J=10.51 Hz, 3.73 Hz, 1H), 3.81 (m, 1H), 3.63 (m, 2H), 3.51 (m, 1H), 2.67 (m, 3H), 2.12 (m, 2H), 1.97 (m, 1H), 1.53 (m, 1H).

EXAMPLE 4A ethyl 1-(2,4-dimethoxybenzyl)-7-(2-(S)-hydroxymethyl-azetidin-1-yl)-4-oxo-1,4-dihydro-[1,8]naphthyridine-3-carboxylate A mixture of EXAMPLE 1B (1.6 g), (S)-(2-hydroxymethyl)azetidine hydrochloride (660 mg), and diisopropylethylamine (4 mL) in acetonitrile (25 mL) at 25° C. was stirred for 3.5 days, treated with water, and filtered. The filtrant was flash chromatographed on silica gel with 9:1 dichloromethane/methanol.

EXAMPLE 4B 1-(2,4-dimethoxybenzyl)-7-(2-(S)-hydroxymethyl-azetidin-1-yl)-4-oxo-1,4-dihydro-[1,8]naphthyridine-3-carboxylic acid A mixture of EXAMPLE 4A (1 g) and 0.1M lithium hydroxide (40 mL) in ethanol (50 mL) was stirred for 24 hours, adjusted to pH 4 with 1M hydrochloric acid, treated with water, and filtered.

EXAMPLE 4C (2aS)-9-(2,4-dimethoxybenzyl)-6-oxo-1,2,2a,3,6,9-hexahydroazeto[1',2':4,5][1,4]oxazino[3,2-b][1,8]-naphthyridine-7-carboxylic acid 60% oily sodium hydride (340 mg) in N,N-dimethylformamide (40 mL) was treated with EXAMPLE 4B (875 mg) in N,N-dimethylformamide (10 mL), heated at 100° C. for 90 minutes, cooled, stirred for 2.5 days, treated with water, adjusted to pH 4 with 1M hydrochloric acid, and filtered.

EXAMPLE 4D (2aS)-6-oxo-1,2,2a,3,6,9-hexahydroazeto[1',2':4,5][1,4]-oxazino[3,2-b][1,8]naphthyridine-7-carboxylic acid EXAMPLE 4C (240 mg) in trifluoroacetic acid (12 mL) at 25° C. was stirred for 1 hour and concentrated. The concentrate was treated with water, and filtered. $^1$H NMR (DMSO-$d_6$) δ 15.3 (br s, 1H), 12.8 (br s, 1H), 8.4 (m, 1H), 7.6 (m, 1H), 4.8 (m, 1H), 4.5 (m, 2H), 4.3 (m, 1H), 3.7 (m, 1H), 2.6 (m, 1H), 2.5 (m, 1H).

EXAMPLE 5A ethyl 1-(2,4-dimethoxybenzyl)-7-(2-hydroxymethylpiperidin-1-yl)-4-oxo-1,4-dihydro-[1,8]naphthyridine-3-carboxylate A mixture of EXAMPLE 1B (2.15 g), piperidinylmethanol (890 mg) and diisopropylethylamine (2.5 mL) in acetonitrile (50 mL) at 25° C. was stirred for 24 hours, heated at 75° C. for 5 days, cooled, treated with water, and extracted with dichloromethane (200 mL). The extract was washed with water and 1M hydrochloric acid and concentrated.

EXAMPLE 5B 1-(2,4-dimethoxybenzyl)-7-(2-(R)-hydroxymethyl-piperidin-1-yl)-4-oxo-1,4-dihydro-[1,8]naphthyridine-3-carboxylic acid A mixture of EXAMPLE 5A (2.3 g) and 0.1M lithium hydroxide (90 mL) in ethanol (110 mL) was stirred for 16 hours, adjusted to pH 3 with 1M hydrochloric acid, treated with water, and extracted with dichloromethane. The extract was concentrated, and the concentrate was recrystallized from ethyl acetate/hexanes.

EXAMPLE 5C (4aR)-11-(2,4-dimethoxybenzyl)-8-oxo-1,2,3,4,4a,5,8,11-octahydropyrido-[1',2':4,5][1,4]oxazino[3,2-b][1,8]naphthyridine-8-carboxylic acid EXAMPLE 5B (1 g) in N,N-dimethylformamide (50 mL) at 0° C. was treated with 60% oily sodium hydride (216 mg), stirred for 30 minutes, heated at 90° C. for 24 hours, cooled, treated with dimethylsulfoxide (20 mL) and 60% oily sodium hydride (63 mg), heated at 90° C. for 14 hours, cooled, treated with water, adjusted to pH 4 with 1M hydrochloric acid, and filtered. The filtrant was recrystallized from ethyl acetate/hexanes.

EXAMPLE 5D 8-oxo-1,2,3,4,4a,5,8,11-octahydropyrido-[1',2':4,5][1,4]oxazino[3,2-b][1,8]naphthyridine-8-carboxylic acid EXAMPLE 5C (217 mg) in trifluoroacetic acid (10 mL) at 25° C. was stirred for 18 hours and concentrated. The concentrate was triturated with acetone then dichloromethane, and filtered. $^1$H NMR (500 MHz, DMSO-$d_6$) δ 12.6 (m, 1H), 8.3 (m, 1H), 7.5 (m, 1H), 4.8 (d, J=13.43 Hz, 1H), 4.3 (dd, J=10.99 Hz, 3.05 Hz, 1H), 4.0 (dd, J=10.99 Hz, 7.32 Hz, 1H), 3.6 (m, 1H), 2.9 (t, J=12.82 Hz, 1H), 1.8 (m, 3H), 1.5 (m, 2H), 1.3 (m, 1H).

EXAMPLE 6A hydroxy-L-prolinol

This compound was prepared as described in Ceulemans, G. et al., Collect. Czech. Chem. Commun. 61; 1996; S234-S237H.

EXAMPLE 6B methyl 1-(2,4-dimethoxybenzyl)-6-fluoro-7-((2S, 4R)-4-hydroxy-2-(hydroxymethyl)pyrrolidinyl)-4-oxo-1,4-dihydro[1,8]naphthyridine-3-carboxylate and methyl 1-(2,4-dimethoxybenzyl)-6-fluoro-7-[(2S,4R)-4-hydroxy-2-(hydroxymethyl)pyrrolidinyl]-4-oxo-1,4-dihydro[1,8]naphthyridine-3-carboxylate A mixture of EXAMPLE 1B (2.26 g), EXAMPLE 6A (1.25 g) and triethylamine (2.25 mL) in acetonitrile (54 mL) at 25° C. was stirred for 18 hours and concentrated. The concentrate was flash chromatographed on silica gel with a gradient from 100% dichloromethane to 8:2 dichloromethane/methanol.

EXAMPLE 6C 1-(2,4-dimethoxybenzyl)-6-fluoro-7-((2S,4R)-4-hydroxy-2-(hydroxymethyl)pyrrolidinyl)-4-oxo-1,4-dihydro[1,8]naphthyridine-3-carboxylic acid A mixture of EXAMPLE 6B (1.13 g) and 1M sodium hydroxide (6.8 mL) in methanol (50 mL) was stirred for 18 hours, treated with water, adjusted to pH 3 with 1M hydrochloric acid, and filtered.

EXAMPLE 6D (2R,3aS)-10-(2,4-dimethoxybenzyl)-2-hydroxy-7-oxo-2,3,3a,4,7,10-hexahydro-1H-pyrrolo[1',2':4,5]-[1,4]oxazino[3,2-b][1,8]naphthyridine-8-carboxylic acid EXAMPLE 6C (507 mg) in N,N-dimethylformamide (21 mL) at 0° C. was treated with 60% oily sodium hydride (172 mg), stirred for 30 minutes, heated at 105° C. for 6 days, cooled, treated with water, adjusted to pH 3.5 with 1M hydrochloric acid, and filtered. The filtrant was flash chromatographed on silica gel with a gradient from 100% dichloromethane to 9:1 dichloromethane/methanol.

EXAMPLE 6E (2R,3aS)-2-hydroxy-7-oxo-2,3,3a,4,7,10-hexahydro-1H-pyrrolo[1',2':4,5][1,4]oxazino[3,2-b][1,8]naphthyridine-8-carboxylic acid EXAMPLE 6D (267 mg) in trifluoroacetic acid (5 mL) was heated at 55° C. for 1 hour and cooled, stirred for 18 hours, and concentrated. The concentrate was dissolved in water (300 mL), and this solution was treated with 1M sodium hydroxide (1.36 mL), sonicated for 2 hours, washed with diethyl ether, adjusted to pH 3.5 with 1M hydrochloric acid, and filtered. $^1$H NMR (300 MHz, DMSO-$d_6$) δ 13.16 (m, 1H), 8.37 (d, J=4.07 Hz, 2H), 7.53 (m, 1H), 4.67 (dd, J=10.51 Hz, 3.73 Hz, 1H), 4.49 (m, 1H), 4.08 (m, 1H), 3.68 (m, 4H), 2.07 (dd, J=12.55 Hz, 5.09 Hz, 1H), 1.67 (m, 1H).

EXAMPLE 7A pyrrolidin-2-ylmethyl triphenylmethylamine

Pyrrolidin-2-ylmethylamine (527 mg) in dichloromethane (10 mL) was treated with triphenylmethyl chloride (1.47 g) and triethylamine (1.5 mL), stirred for 3 hours, treated with dichloromethane, washed with water, saturated NaHCO$_3$, and water, and concentrated. The concentrate was flash chromatographed on silica gel with a gradient of 3%-10% methanol in 99:1 dichloromethane/triethylamine. $^1$H NMR (DMSO-$d_6$) δ 7.4 (m, 6H), 7.3 (m, 6H), 7.2 (m, 3H), 3.2 (m, 1H), 2.8-2.5 (m, 2H), 2.0 (m, 1H), 1.9 (m, 1H), 1.7 (m, 1H), 1.5 (m, 2H), 1.2 (m, 1H).

EXAMPLE 7B ethyl 1-(2,4-dimethoxybenzyl)-6-fluoro-4-oxo-7-(2-((trityl-amino)methyl)pyrrolidin-1-yl)-1,4-dihydro[1, 8]-naphthyridine-3-carboxylate A mixture of EXAMPLE 7A (g), EXAMPLE 1B (1.6 g), and diisopropylethylamine (2.1 mL) in acetonitrile (35 mL) at 25° C. was stirred for 16 hours, treated with water, and extracted with dichloromethane. The extract was washed with saturated NaHCO$_3$ and water, and concentrated. The concentrate was flash chromatographed on silica gel with 95:5 dichloromethane/methanol.

EXAMPLE 7C 1-(2,4-dimethoxybenzyl)-6-fluoro-4-oxo-7-(2-[(trityl-amino)methyl]-pyrrolidin-1-yl)-1,4-dihydro[1,8]-naphthyridine-3-caboxylic acid A mixture of EXAMPLE 7B (1.7 g) and 0.1M lithium hydroxide (40 mL) in ethanol (80 mL) was stirred for 18 hours, adjusted to pH 5 with 1M hydrochloric acid, and filtered.

EXAMPLE 7D 7-(2-aminomethylpyrrolidin-1-yl)-1-(2,4-dimethoxybenzyl)-6-fluoro-4-oxo-1,4-dihydro-[1,8]naphthyridine-3-caboxylic acid EXAMPLE 7C (500 mg) in acetone (15 mL) was treated with three drops of concentrated hydrochloric acid, stirred at 25° C. for 18 hours, and filtered.

EXAMPLE 7E (3aS)-10-(2,4-dimethoxybenzyl)-7-oxo-1,2,3,3a,4,5, 7,10-octahydropyrrolo[2',1':6,1]pyrazino[2,3-b][1,8] naphthyridine-8-carboxylic acid EXAMPLE 7D (375 mg) in N,N-dimethylformamide (30 mL) at 140° C. was stirred for 1 hour and at 100° C. for 3 days, cooled, treated with water, and extracted with ethyl acetate. The extract was concentrated and flash chromatographed on silica gel with 95:5 dichloromethane/methanol. $^1$H NMR (300 MHz, DMSO-$d_6$) δ 16.4 (m, 1H), 8.7 (m, 1H), 7.3 (d, J=8.09 Hz, 1H), 7.2 (m, 1H), 6.5 (m, 2H), 5.5 (m, 2H), 3.8 (m, 3H), 3.7 (m,3H), 3.6 (m, 4H), 2.7 (t, J=10.30 Hz, 1H), 2.1 (m, 2H), 2.0 (m, 1H), 1.5 (m, 1H).

EXAMPLE 7F (3aS)-7-oxo-1,2,3,3a,4,5,7,10-octahydropyrrolo-[2', 1':6,1]pyrazino[2,3-b][1,8]naphthyridine-8-carboxylic acid EXAMPLE 7E (60 mg) in trifluoroacetic acid (3 mL) at 70° C. was stirred for 1.5 hours, cooled and concentrated. The concentrate was azeotroped with toluene and dissolved in dichloromethane. This solution was washed with water and concentrated. The concentrate was flash chromatographed on silica gel with 95:5 dichloromethane/methanol. $^1$H NMR (500 MHz, DMSO-$d_6$) δ 8.2 (m, 1H), 7.2 (m, 1H), 6.5 (m, 1H), 6.0 (m, 1H), 3.7 (m, 4H), 2.7 (t, J=10.38 Hz, 1H), 2.1 (m, 1H), 2.1 (m, 1H), 1.9 (m, 1H), 1.5 (m, 1H)

EXAMPLE 7G (3aS)-10-(2,4-dimethoxybenzyl)-5-methyl-7-oxo-1,2,3,3a,4,5,7,10-octahydropyrrolo[2',1':6,1]pyrazino[2,3-b][1,8]naphthyridine-8-carboxylic acid EXAMPLE 7E (80 mg) in N,N-dimethylformamide (3 mL) at 25° C. was treated with 60% oily sodium hydride (17 mg), stirred for 1 hour, treated with 60% oily sodium hydride (15 mg), stirred for 30 minutes, treated with methyl iodide (100 µL), stirred for 2.5 days, treated with water, and extracted with ethyl acetate. The extract was washed with water and concentrated. The concentrate was flash chromatographed on silica gel with 95:5 dichloromethane/methanol.

EXAMPLE 7H (3aS)-5-methyl-7-oxo-1,2,3,3a,4,5,7,10-octahydro-pyrrolo-[2',1':6,1]pyrazino[2,3-b][1,8]naphthyridine-8-carboxylic acid EXAMPLE 7G (41 mg) in trifluoroacetic acid (2 mL) at 25° C. was stirred for 16 hours and concentrated. The concentrate in 1M sodium hydroxide (2 mL) was stirred for 18 hours, treated with water, acidified with 1M hydrochloric acid, and extracted with dichloromethane. The extract was concentrated and flash chromatographed on silica gel with 95:5 dichloromethane/methanol. $^1$H NMR (300 MHz, DMSO-$d_6$) δ 16.5 (m, 1H), 13.0 (br s, 1H), 8.2 (m, 1H), 7.0 (m, 1H), 3.9 (m, 1H), 3.6 (m, 3H), 2.9 (m, 3H), 2.7 (t, J=10.30 Hz, 1H), 2.2 (m, 1H), 2.1 (m, 1H), 1.9 (m, 1H), 1.5 (m, 1H).

These examples are merely illustrative of this invention and are not intended to limit the same to the specifically embodied compounds and processes. Variations and changes which are obvious to one skilled in the art are intended to be within the scope of this invention as defined in the appended claims.

What is claimed is:

1. A compound having the formula (I) or salt thereof:

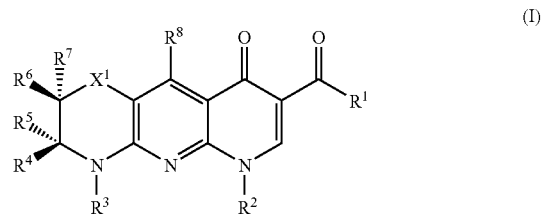

in which $R^1$ is —OH, or O—$R^9$, $NH_2$, or N—$R^9$; $R^2$ is H, allyloxy, 2,4-dimethoxybenzyl, 2-cyanoethyl, 4-methoxybenzyl, trimethylsilyl, tert-butyl, and triphenylmethyl; $R^3$ and $R^4$ combine to form $(CH_2)n$ with n=1, 2, 3; $R^5$-$R^8$ is H; $R^9$ is $C_1$-alkyl, $C_2$-alkyl, $C_3$-alkyl, $C_4$-alkyl, $C_5$-alkyl, or $C_6$-alkyl; and $X_1$ is O, NH, and N-unsubstituted alkyl.

2. A method for treating bacterial infections in a fish or a mammal comprising administering to a fish or mammal in need thereof a therapeutically effective amount of the compound of claim 1.

* * * * *